US008026360B2

(12) United States Patent
Kamboj et al.

(10) Patent No.: US 8,026,360 B2
(45) Date of Patent: Sep. 27, 2011

(54) SUBSTITUTED PYRIDAZINES AS STEAROYL-COA DESATURASE INHIBITORS

(75) Inventors: Rajender Kamboj, Burnaby (CA); Zaihui Zhang, Vancouver (CA); Jianmin Fu, Coquitlam (CA); Vandna Raina, Gurgaon (IN); Serguei Sviridov, Burnaby (CA); Vishnumurthy Kodumuru, Burnaby (CA); Nagasree Chakka, Burnaby (CA); Shifeng Lui, Port Coquitlam (CA); Shaoyi Sun, Coquitlam (CA); Duanjie Hou, Burnaby (CA)

(73) Assignee: Xenon Pharmaceuticals Inc., Burnaby, BC (CA)

( * ) Notice: Subject to any disclaimer, the term of this patent is extended or adjusted under 35 U.S.C. 154(b) by 86 days.

(21) Appl. No.: 12/541,005

(22) Filed: Aug. 13, 2009

(65) Prior Publication Data
US 2009/0306090 A1 Dec. 10, 2009

Related U.S. Application Data

(62) Division of application No. 11/575,641, filed as application No. PCT/US2005/033801 on Sep. 20, 2005, now Pat. No. 7,592,343.

(60) Provisional application No. 60/611,643, filed on Sep. 20, 2004.

(51) Int. Cl.
*C07D 401/00* (2006.01)
(52) U.S. Cl. ...... 544/238; 544/284; 544/359; 546/268.1; 548/152; 548/257; 548/470
(58) Field of Classification Search .......... 544/238, 544/284, 359; 546/268.1; 548/152, 257, 548/470
See application file for complete search history.

(56) References Cited

U.S. PATENT DOCUMENTS

| | | | |
|---|---|---|---|
| 2,985,657 A | 5/1961 | Janssen | 260/256.4 |
| 3,538,097 A | 11/1970 | Loewe et al. | 260/268 |
| 3,830,924 A | 8/1974 | Berkelhammer et al. | 424/270 |
| 3,975,384 A | 8/1976 | Narr et al. | 260/243 R |
| 4,026,891 A | 5/1977 | Austel et al. | 260/250 AH |
| 4,247,551 A | 1/1981 | Bellasio et al. | 424/248.56 |
| 4,435,401 A | 3/1984 | Campbell et al. | 424/251 |
| 4,439,606 A | 3/1984 | Du et al. | 544/356 |
| 4,459,296 A | 7/1984 | Ancher et al. | 424/244 |
| 5,001,125 A | 3/1991 | Stokbroekx et al. | 514/252 |
| 5,166,147 A | 11/1992 | Earl | 514/252 |
| 5,286,728 A | 2/1994 | Ferrini | 514/255 |
| 5,310,499 A | 5/1994 | Scherowsky et al. | 252/299.61 |
| 5,334,328 A | 8/1994 | Scherowsky et al. | 252/299.61 |
| 5,380,726 A | 1/1995 | Ferrini | 514/255 |
| 5,384,070 A | 1/1995 | Hemmerling et al. | 252/299.61 |
| 5,463,071 A | 10/1995 | Himmelsbach et al. | 548/251 |
| 5,494,908 A | 2/1996 | O'Malley et al. | 514/228.2 |
| 5,512,207 A | 4/1996 | Manero et al. | 252/299.61 |
| 5,527,763 A | 6/1996 | Miyazaki et al. | 504/242 |
| 5,547,605 A | 8/1996 | Fuss et al. | 252/299.6 |
| 5,637,592 A | 6/1997 | Heeres et al. | 514/252 |
| 5,668,148 A | 9/1997 | Payne et al. | 514/314 |
| 5,719,154 A | 2/1998 | Tucker et al. | 514/252 |
| 5,728,700 A | 3/1998 | Heeres et al. | 514/252 |
| 5,847,149 A | 12/1998 | Fuss et al. | 548/136 |
| 5,849,759 A | 12/1998 | Arnaiz et al. | 514/322 |
| 5,874,023 A | 2/1999 | Manero et al. | 252/299.61 |
| 5,882,546 A | 3/1999 | Manero et al. | 252/299.62 |
| 5,904,877 A | 5/1999 | Manero et al. | 252/299.62 |
| 5,911,913 A | 6/1999 | Manero et al. | 252/299.61 |
| 5,942,618 A | 8/1999 | Manero et al. | 546/139 |
| 5,965,761 A | 10/1999 | Buchecker et al. | 556/440 |
| 5,985,878 A | 11/1999 | Stokbroekx et al. | 514/252 |
| 5,994,356 A | 11/1999 | Pieper et al. | 514/252 |
| 5,998,412 A | 12/1999 | Broka et al. | 514/250 |
| 6,127,382 A | 10/2000 | Beard et al. | 514/311 |
| 6,156,758 A | 12/2000 | Kung et al. | 514/260 |
| 6,245,916 B1 | 6/2001 | Fauchere et al. | 548/263.8 |
| 6,251,911 B1 | 6/2001 | Bold et al. | 514/258 |
| 6,372,746 B1 | 4/2002 | Corbera-Arjona et al. | 514/252.14 |

(Continued)

FOREIGN PATENT DOCUMENTS
CA 2052510 A1 4/1992

(Continued)

OTHER PUBLICATIONS

Attie et al., "Relationship between stearoyl-CoA desaturase activity and plasma triglycerides in human and mouse hypertriglyceridemia," *Journal of Lipid Research* 43: 1899-1907, 2002.
Boissier et al., "Synthesis and Pharmacological Study of New Piperazine Derivatives. I. Benzylpiperazines," *Journal of Medicinal Chemistry* 6 541-544, Sep. 1963.
Charles River Laboratories, "ZDF Rat," URL=http://www.criver.com/research_models_and_services/research_models/ZDF.html, download date Mar. 17, 2008.
Cohen et al., "Role for Stearoyl-CoA Desaturase-1 in Leptin-Mediated Weight Loss," *Science* 297: 240-243, Jul. 12, 2002.

(Continued)

*Primary Examiner* — James O Wilson
*Assistant Examiner* — Douglas M Willis
(74) *Attorney, Agent, or Firm* — Seed IP Law Group PLLC

(57) ABSTRACT

Methods of treating an SCD-mediated disease or condition in a mammal, preferably a human, are disclosed, wherein the methods comprise administering to a mammal in need thereof a compound of formula (I):

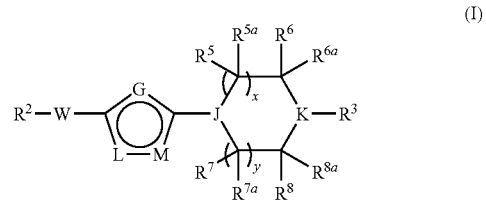

(I)

where x, y, G, J, K, L, M, W, $R^2$, $R^3$, $R^5$, $R^{5a}$, $R^6$, $R^{6a}$, $R^7$, $R^{7a}$, $R^8$ and $R^{8a}$ are defined herein. Pharmaceutical compositions comprising the compounds of formula (I) are also disclosed.

5 Claims, No Drawings

U.S. PATENT DOCUMENTS

| | | |
|---|---|---|
| 6,441,000 B1 | 8/2002 | Gibson et al. ............... 514/322 |
| 6,482,479 B1 | 11/2002 | Dübal et al. ................ 428/1.1 |
| 6,500,956 B1 | 12/2002 | Geissler et al. ............. 546/257 |
| 6,562,827 B1 | 5/2003 | Lubisch et al. ......... 514/252.13 |
| 6,562,847 B1 | 5/2003 | Lee .............................. 514/343 |
| 6,620,811 B2 | 9/2003 | Flohr et al. ............... 514/233.8 |
| 6,627,630 B1 | 9/2003 | Kawano et al. ............ 514/248 |
| 6,677,452 B1 | 1/2004 | Chen et al. ................. 544/365 |
| 6,911,447 B2 | 6/2005 | Mazur et al. ........... 514/253.05 |
| 6,916,812 B2 | 7/2005 | Poindexter et al. ....... 514/235.8 |
| 7,064,215 B2 | 6/2006 | Renhowe et al. ........... 548/125 |
| 7,115,607 B2 | 10/2006 | Fotsch et al. ........... 514/252.13 |
| 7,125,877 B2 | 10/2006 | Kobayashi et al. ...... 514/254.06 |
| 7,160,878 B2 | 1/2007 | Herron et al. ............... 514/218 |
| 7,220,736 B2 | 5/2007 | Yamada et al. ........... 514/211.1 |
| 7,220,744 B2 | 5/2007 | Jolidon et al. ........... 514/235.8 |
| 7,294,626 B2 | 11/2007 | Hohlweg ............... 514/252.02 |
| 7,319,099 B2 | 1/2008 | Jolidon et al. .............. 514/245 |
| 7,335,658 B2 | 2/2008 | Chakka et al. ......... 514/252.02 |
| 7,345,043 B2 | 3/2008 | Anandan et al. ........ 514/254.02 |
| 7,390,813 B1 | 6/2008 | Gray-Keller et al. ........ 514/255 |
| 7,399,765 B2 | 7/2008 | Bunnelle et al. ........ 514/252.06 |
| 7,423,030 B2 | 9/2008 | Augereau et al. ....... 514/210.21 |
| 7,491,729 B2 | 2/2009 | Bakker et al. ............... 514/267 |
| 7,547,698 B2 | 6/2009 | Kamboj et al. ............. 514/248 |
| 7,572,796 B2 | 8/2009 | Schadt et al. ........... 514/254.09 |
| 7,595,316 B2 | 9/2009 | Ohtake et al. .............. 514/247 |
| 7,632,950 B2 | 12/2009 | Kuwabara et al. ........... 546/255 |
| 7,662,819 B2 | 2/2010 | Chisholm et al. ........... 514/249 |
| 7,767,677 B2 | 8/2010 | Kamboj et al. .......... 514/252.02 |
| 7,777,036 B2 | 8/2010 | Kamboj et al. .............. 544/367 |
| 7,829,712 B2 | 11/2010 | Kamboj et al. .............. 544/367 |
| 2002/0045613 A1 | 4/2002 | Pauls et al. ............... 514/210.18 |
| 2002/0198237 A1 | 12/2002 | Bogenstaetter et al. ....... 514/326 |
| 2003/0106169 A1 | 6/2003 | Vidal et al. ........................ 8/405 |
| 2003/0127627 A1 | 7/2003 | Amakawa et al. ........ 252/299.01 |
| 2003/0157552 A1 | 8/2003 | Hayden et al. ................. 435/7.1 |
| 2003/0166932 A1 | 9/2003 | Beard et al. ................... 544/238 |
| 2003/0203893 A1 | 10/2003 | Barth et al. .................. 514/215 |
| 2003/0225076 A1 | 12/2003 | Biwersi et al. ............. 514/230.5 |
| 2003/0225097 A1 | 12/2003 | Block et al. .............. 514/252.01 |
| 2004/0082586 A1 | 4/2004 | Plant et al. ................ 514/252.05 |
| 2004/0087577 A1 | 5/2004 | Pratt et al. .................. 514/222.8 |
| 2004/0092524 A1 | 5/2004 | Perez et al. .................. 514/249 |
| 2004/0097492 A1 | 5/2004 | Pratt et al. .................. 514/222.8 |
| 2004/0116417 A1 | 6/2004 | Boubia et al. ............... 514/227.8 |
| 2004/0147573 A1 | 7/2004 | Eriksson et al. .............. 514/369 |
| 2004/0176380 A1 | 9/2004 | Hoffmann et al. ............. 514/251 |
| 2004/0192701 A1 | 9/2004 | Iwata et al. .............. 514/253.09 |
| 2004/0220171 A1 | 11/2004 | Pauls et al. ................ 514/210.2 |
| 2004/0220191 A1 | 11/2004 | Schwink et al. ......... 514/252.03 |
| 2005/0014765 A1 | 1/2005 | Mailliet et al. ........... 514/254.02 |
| 2005/0014942 A1 | 1/2005 | Maruyama et al. ........... 544/183 |
| 2005/0020593 A1 | 1/2005 | Mailliet et al. ............... 514/243 |
| 2005/0059668 A1 | 3/2005 | Alberati-Giani et al. ........................ 514/252.13 |
| 2005/0065143 A1 | 3/2005 | Chakka et al. ............... 514/218 |
| 2005/0075345 A1 | 4/2005 | Heymans et al. ........ 514/254.02 |
| 2005/0119251 A1 | 6/2005 | Fu et al. ....................... 514/218 |
| 2005/0124660 A1 | 6/2005 | Antel et al. ................... 514/326 |
| 2005/0130989 A1 | 6/2005 | Le-Brun et al. .......... 514/254.05 |
| 2005/0234046 A1 | 10/2005 | Zhao et al. .................. 514/218 |
| 2006/0009459 A1 | 1/2006 | Chakka et al. ........... 514/252.01 |
| 2007/0082908 A1 | 4/2007 | Nakahira et al. ............. 514/243 |
| 2007/0299081 A1 | 12/2007 | Kamboj et al. .......... 514/252.03 |
| 2008/0015230 A1 | 1/2008 | Kamboj et al. .............. 514/332 |
| 2008/0096895 A1 | 4/2008 | Kamboj et al. .......... 514/252.02 |
| 2008/0108629 A1 | 5/2008 | Kamboj et al. .......... 514/254.03 |
| 2008/0167321 A1 | 7/2008 | Kamboj et al. .......... 514/253.13 |
| 2008/0188488 A1 | 8/2008 | Kamboj et al. .......... 514/255.03 |
| 2008/0207587 A1 | 8/2008 | Kamboj et al. .......... 514/210.18 |
| 2009/0197894 A1 | 8/2009 | Fu et al. .................... 514/253.13 |
| 2010/0120779 A1 | 5/2010 | Haydar et al. ................ 514/249 |
| 2010/0152187 A1 | 6/2010 | Fu et al. .................... 514/236.8 |
| 2011/0009414 A9 | 1/2011 | Kamboj et al. ............... 514/248 |

FOREIGN PATENT DOCUMENTS

| | | |
|---|---|---|
| CA | 2114178 A1 | 7/1994 |
| CA | 2469395 A1 | 6/2003 |
| DE | 23 41 925 A1 | 3/1975 |
| DE | 24 27 943 A1 | 1/1976 |
| DE | 27 05 641 A1 | 8/1977 |
| DE | 35 36 030 A1 | 4/1987 |
| DE | 43 43 286 A1 | 6/1995 |
| DE | 44 23 044 A1 | 1/1996 |
| DE | 199 34 799 A1 | 2/2001 |
| DE | 102 59 382 A1 | 7/2004 |
| EP | 0 009 655 A1 | 4/1980 |
| EP | 0 055 583 A1 | 7/1982 |
| EP | 0 200 024 A2 | 11/1986 |
| EP | 0 300 526 A2 | 1/1989 |
| EP | 0 320 032 A1 | 6/1989 |
| EP | 0 385 350 B1 | 9/1990 |
| EP | 0 156 433 B1 | 2/1991 |
| EP | 0 438 230 B1 | 7/1991 |
| EP | 0 524 146 A1 | 1/1993 |
| EP | 0 533 344 A1 | 3/1993 |
| EP | 0 548 798 A1 | 6/1993 |
| EP | 0 606 824 A1 | 7/1994 |
| EP | 0 211 457 A2 | 2/1997 |
| EP | 0 927 992 A1 | 7/1999 |
| EP | 1 035 115 B1 | 9/2000 |
| EP | 1 048 652 A1 | 11/2000 |
| EP | 1 156 045 A1 | 11/2001 |
| EP | 1 180 514 A1 | 2/2002 |
| EP | 1 184 442 A1 | 3/2002 |
| EP | 1 243 268 A1 | 9/2002 |
| EP | 1 277 729 A1 | 1/2003 |
| EP | 1 375 495 A1 | 1/2004 |
| EP | 1 386 915 A1 | 2/2004 |
| EP | 1 396 487 A1 | 3/2004 |
| EP | 1 452 525 A1 | 9/2004 |
| EP | 1 452 530 A1 | 9/2004 |
| FR | 2 273 545 A1 | 1/1976 |
| FR | 2 868 780 A1 | 10/2005 |
| GB | 2 136 801 A | 9/1984 |
| JP | 10007572 A | 1/1998 |
| JP | 2004-203871 A | 7/2004 |
| WO | WO 88/07527 A1 | 10/1988 |
| WO | WO 88/08424 A1 | 11/1988 |
| WO | WO 91/09594 A1 | 7/1991 |
| WO | WO 91/09849 A1 | 7/1991 |
| WO | WO 92/18478 A1 | 10/1992 |
| WO | WO 93/00313 A2 | 1/1993 |
| WO | WO 93/01181 A1 | 1/1993 |
| WO | WO 93/14077 A1 | 7/1993 |
| WO | WO 93/18016 A1 | 9/1993 |
| WO | WO 94/07856 A1 | 4/1994 |
| WO | WO 94/12495 A1 | 6/1994 |
| WO | WO 94/26720 A1 | 11/1994 |
| WO | WO 93/25550 A1 | 12/1994 |
| WO | WO 95/25443 A1 | 9/1995 |
| WO | WO 96/01818 A1 | 1/1996 |
| WO | WO 96/01821 A1 | 1/1996 |
| WO | WO 96/01822 A1 | 1/1996 |
| WO | WO 96/11210 A1 | 4/1996 |
| WO | WO 96/33251 A1 | 10/1996 |
| WO | WO 97/03054 A1 | 1/1997 |
| WO | WO 97/21708 A1 | 6/1997 |
| WO | WO 97/26258 A1 | 7/1997 |
| WO | WO 97/28128 A1 | 8/1997 |
| WO | WO 97/37975 A1 | 10/1997 |
| WO | WO 98/01446 A1 | 1/1998 |
| WO | WO 98/04544 A1 | 2/1998 |
| WO | WO 98/14450 A1 | 4/1998 |
| WO | WO 99/00386 A1 | 1/1999 |
| WO | WO 99/14212 A1 | 3/1999 |
| WO | WO 99/20606 A2 | 4/1999 |
| WO | WO 99/21834 A1 | 5/1999 |
| WO | WO 99/41244 A1 | 8/1999 |
| WO | WO 99/43671 A1 | 9/1999 |
| WO | WO 99/47507 A2 | 9/1999 |
| WO | WO 99/54305 A1 | 10/1999 |
| WO | WO 99/55675 A1 | 11/1999 |
| WO | WO 99/58526 A1 | 11/1999 |

| | | | | | | |
|---|---|---|---|---|---|---|
| WO | WO 99/64416 A2 | 12/1999 | | WO | WO 03/091247 A2 | 11/2003 |
| WO | WO 99/64417 A2 | 12/1999 | | WO | WO 03/092678 A1 | 11/2003 |
| WO | WO 00/21959 A1 | 4/2000 | | WO | WO 03/092686 A1 | 11/2003 |
| WO | WO 00/25768 A1 | 5/2000 | | WO | WO 03/095432 A1 | 11/2003 |
| WO | WO 00/32193 A1 | 6/2000 | | WO | WO 03/106456 A2 | 12/2003 |
| WO | WO 00/32582 A1 | 6/2000 | | WO | WO 2004/000318 A2 | 12/2003 |
| WO | WO 00/44755 A1 | 8/2000 | | WO | WO 2004/000820 A1 | 12/2003 |
| WO | WO 00/47553 A1 | 8/2000 | | WO | WO 2004/009587 A1 | 1/2004 |
| WO | WO 00/55139 A2 | 9/2000 | | WO | WO 2004/010927 A2 | 2/2004 |
| WO | WO 00/59509 A1 | 10/2000 | | WO | WO 2004/011418 A1 | 2/2004 |
| WO | WO 00/66578 A1 | 11/2000 | | WO | WO 2004/011430 A1 | 2/2004 |
| WO | WO 00/69987 A1 | 11/2000 | | WO | WO 2004/014871 A1 | 2/2004 |
| WO | WO 00/71536 A1 | 11/2000 | | WO | WO 2004/022061 A1 | 3/2004 |
| WO | WO 01/07409 A1 | 2/2001 | | WO | WO 2004/022556 A1 | 3/2004 |
| WO | WO 01/17942 A1 | 3/2001 | | WO | WO 2004/022559 A1 | 3/2004 |
| WO | WO 01/19798 A2 | 3/2001 | | WO | WO 2004/026863 A1 | 4/2004 |
| WO | WO 01/19822 A1 | 3/2001 | | WO | WO 2004/026865 A1 | 4/2004 |
| WO | WO 01/22938 A1 | 4/2001 | | WO | WO 2004/035549 A1 | 4/2004 |
| WO | WO 01/32628 A1 | 5/2001 | | WO | WO 2004/037809 A1 | 5/2004 |
| WO | WO 01/44213 A1 | 6/2001 | | WO | WO 2004/039780 A1 | 5/2004 |
| WO | WO 01/46164 A1 | 6/2001 | | WO | WO 2004/046130 A1 | 6/2004 |
| WO | WO 01/47921 A1 | 7/2001 | | WO | WO 2004/048321 A1 | 6/2004 |
| WO | WO 01/60369 A1 | 8/2001 | | WO | WO 2004/058727 A1 | 7/2004 |
| WO | WO 01/60458 A2 | 8/2001 | | WO | WO 2004/065378 A1 | 8/2004 |
| WO | WO 01/62233 A2 | 8/2001 | | WO | WO 2004/065380 A1 | 8/2004 |
| WO | WO 01/62954 A2 | 8/2001 | | WO | WO 2004/069227 A1 | 8/2004 |
| WO | WO 01/64646 A2 | 9/2001 | | WO | WO 2004/069792 A2 | 8/2004 |
| WO | WO 01/68619 A1 | 9/2001 | | WO | WO 2004/069812 A1 | 8/2004 |
| WO | WO 01/70668 A2 | 9/2001 | | WO | WO 2004/074253 A1 | 9/2004 |
| WO | WO 01/81310 A1 | 11/2001 | | WO | WO 2004/074266 A1 | 9/2004 |
| WO | WO 01/83460 A1 | 11/2001 | | WO | WO 2004/076413 A2 | 9/2004 |
| WO | WO 01/96323 A1 | 12/2001 | | WO | WO 2004/078716 A1 | 9/2004 |
| WO | WO 01/96327 A1 | 12/2001 | | WO | WO 2004/089416 A2 | 10/2004 |
| WO | WO 01/97810 A2 | 12/2001 | | WO | WO 2004/096810 A1 | 11/2004 |
| WO | WO 02/08221 A2 | 1/2002 | | WO | WO 2004/101581 A2 | 11/2004 |
| WO | WO 02/26944 A2 | 4/2002 | | WO | WO 2004/108676 A1 | 12/2004 |
| WO | WO 02/30405 A2 | 4/2002 | | WO | WO 2004/110350 A2 | 12/2004 |
| WO | WO 02/30927 A1 | 4/2002 | | WO | WO 2004/114118 A1 | 12/2004 |
| WO | WO 02/32857 A1 | 4/2002 | | WO | WO 2005/003087 A2 | 1/2005 |
| WO | WO 02/46151 A1 | 6/2002 | | WO | WO 2005/007644 A1 | 1/2005 |
| WO | WO 02/46170 A2 | 6/2002 | | WO | WO 2005/009976 A1 | 2/2005 |
| WO | WO 02/055012 A2 | 7/2002 | | WO | WO 2005/009980 A1 | 2/2005 |
| WO | WO 02/055013 A2 | 7/2002 | | WO | WO 2005/011653 A2 | 2/2005 |
| WO | WO 02/055014 A2 | 7/2002 | | WO | WO 2005/011654 A1 | 2/2005 |
| WO | WO 02/055496 A1 | 7/2002 | | WO | WO 2005/011655 A2 | 2/2005 |
| WO | WO 02/066446 A1 | 8/2002 | | WO | WO 2005/011656 A2 | 2/2005 |
| WO | WO 02/072548 A2 | 9/2002 | | WO | WO 2005/011657 A2 | 2/2005 |
| WO | WO 02/074767 A1 | 9/2002 | | WO | WO 2005/011700 A1 | 2/2005 |
| WO | WO 02/081453 A1 | 10/2002 | | WO | WO 2005/012304 A2 | 2/2005 |
| WO | WO 02/083624 A1 | 10/2002 | | WO | WO 2005/012307 A1 | 2/2005 |
| WO | WO 02/088093 A1 | 11/2002 | | WO | WO 2005/014563 A1 | 2/2005 |
| WO | WO 02/096867 A2 | 12/2002 | | WO | WO 2005/016910 A1 | 2/2005 |
| WO | WO 02/096867 A3 | 12/2002 | | WO | WO 2005/021548 A2 | 3/2005 |
| WO | WO 02/102778 A1 | 12/2002 | | WO | WO 2005/021550 A1 | 3/2005 |
| WO | WO 03/003008 A1 | 1/2003 | | WO | WO 2005/023260 A1 | 3/2005 |
| WO | WO 03/011843 A1 | 2/2003 | | WO | WO 2005/023261 A1 | 3/2005 |
| WO | WO 03/016306 A1 | 2/2003 | | WO | WO 2005/028477 A1 | 3/2005 |
| WO | WO 03/018563 A1 | 3/2003 | | WO | WO 2005/028479 A2 | 3/2005 |
| WO | WO 03/022274 A2 | 3/2003 | | WO | WO 2005/030140 A2 | 4/2005 |
| WO | WO 03/035602 A1 | 5/2003 | | WO | WO 2005/030188 A2 | 4/2005 |
| WO | WO 03/037862 A1 | 5/2003 | | WO | WO 2005/032468 A2 | 4/2005 |
| WO | WO 03/037871 A1 | 5/2003 | | WO | WO 2005/034952 A1 | 4/2005 |
| WO | WO 03/037872 A1 | 5/2003 | | WO | WO 2005/037839 A1 | 4/2005 |
| WO | WO 03/040125 A1 | 5/2003 | | WO | WO 2005/039550 A2 | 5/2005 |
| WO | WO 03/043636 A1 | 5/2003 | | WO | WO 2005/040109 A1 | 5/2005 |
| WO | WO 03/045920 A1 | 6/2003 | | WO | WO 2005/040136 A1 | 5/2005 |
| WO | WO 03/045921 A1 | 6/2003 | | WO | WO 2005/044192 A2 | 5/2005 |
| WO | WO 03/050088 A1 | 6/2003 | | WO | WO 2005/044797 A1 | 5/2005 |
| WO | WO 03/051797 A2 | 6/2003 | | WO | WO 2005/049616 A1 | 6/2005 |
| WO | WO 03/066604 A2 | 8/2003 | | WO | WO 2005/049617 A1 | 6/2005 |
| WO | WO 03/075929 A1 | 9/2003 | | WO | WO 2005/060665 A2 | 7/2005 |
| WO | WO 03/076395 A1 | 9/2003 | | WO | WO 2005/063754 A1 | 7/2005 |
| WO | WO 03/076400 A1 | 9/2003 | | WO | WO 2005/115983 A1 | 12/2005 |
| WO | WO 03/076401 A1 | 9/2003 | | WO | WO 2006/009734 A1 | 1/2006 |
| WO | WO 03/076422 A1 | 9/2003 | | WO | WO 2006/014168 A1 | 2/2006 |
| WO | WO 03/076430 A1 | 9/2003 | | WO | WO 2006/033943 A2 | 3/2006 |
| WO | WO 03/078413 A1 | 9/2003 | | WO | WO 2006/034279 A1 | 3/2006 |
| WO | WO 03/080060 A1 | 10/2003 | | WO | WO 2006/034312 A1 | 3/2006 |
| WO | WO 03/087086 A2 | 10/2003 | | WO | WO 2006/034315 A2 | 3/2006 |

| WO | WO 2006/034338 A1 | 3/2006 |
| WO | WO 2006/034341 A2 | 3/2006 |
| WO | WO 2006/034441 A1 | 3/2006 |
| WO | WO 2006/034446 A2 | 3/2006 |
| WO | WO 2006/034440 A2 | 5/2006 |
| WO | WO 2006/072436 A1 | 7/2006 |
| WO | WO 2006/101521 A2 | 9/2006 |
| WO | WO 2006/106423 A2 | 10/2006 |
| WO | WO 2006/130986 A1 | 12/2006 |
| WO | WO 2007/130075 A1 | 11/2007 |

OTHER PUBLICATIONS

Cohen et al., "Stearoyl-CoA Desaturase-1 and the Metabolic Syndrome," *Current Drug Targets: Immune, Endocrine and Metabolic Disorders* 3(4): 271-280, 2003.

de Antueno et al., "Relationship Between Mouse Liver Δ9 Desaturase Activity and Plasma Lipids," *Lipids* 28(4): 285-290, 1993.

Diot et al., "Stearoyl-CoA Desaturase 1 Coding Sequences and Antisense RNA Affect Lipid Secretion in Transfected Chicken LMH Hepatoma Cells," *Archives of Biochemistry and Biophysics* 380(2): 243-250, Aug. 15, 2000.

Dobrzyn and Ntambi, "Stearoyl-CoA desaturase as a new drug target for obesity treatment," *Obesity Reviews* 6: 169-174, 2005.

Dubey et al., "Synthesis and Anthelmintic Activity of 5(6)-(Benzimidazol-2-ylcarbamoyl) and (4-Substituted piperazin-l-yl)benzimidazoles," *J. of Medicinal Chemistry* 28(11): 1748-1750, 1985.

Enser, "Desaturation of Stearic Acid by Liver and Adipose Tissue from Obese-Hyperglycaemic Mice (*ob/ob*)," *Biochem. J.* 148:551-555, 1975.

Flowers et al., "Probing the role of stearoyl-CoA desaturase-1 in hepatic insulin resistance," *The Journal of Clinical Investigation* 116(6): 1478-1481, Jun. 2006.

Foroumadi et al., "Synthesis and evaluation of in vitro antimycobacterial activity of some 5-(5-Nitro-2-thienyl)-2-(piperazinyl, piperidinyl and morpholinyl)-1,3,4-thiadiazole derivatives," *Boll. Chim. Farmac.* 142(9): 416-419, Nov. 2003.

Gooβen and Ghosh, "Palladium-Catalyzed Synthesis of Aryl Ketones from Boronic Acids and Carboxylic Acids Activated in situ by Pivalic Anhydride", *Eur. J. Org. Chem.*: 3254-3267, 2002.

Gotor et al., "Fungal and Bacterial Regioselective Hydroxylation of Pyrimidine Heterocycles," *Tetrahedron* 53(18): 6421-6432, 1997.

Gutiérrez-Juárez, "Critical role of stearoyl-CoA desaturas-1 (SCD1) in the onset of diet-induced hepatic insulin resistance," *The Journal of Clinical Investigation* 116(6): 1686-1695, Jun. 2006.

Hori et al., "Studies on Antitumor-active 2,3-Dioxopiperazine Derivatives. III. Synthesis and Structure-Antitumor Activity Relationship of 1-(4-Aminobenzyl)-2,3-dioxopiperazine Derivatives," *Chem. Pharm. Bull* 29(5): 1253-1266, 1981.

Jacobsen et al., "2-(Aminomethyl)chromans that Inhibit Iron-Dependent Lipid Peroxidation and Protect against Central Nervous System Trauma and Ischemia," *Journal of Medicinal Chemistry* 35(23): 4464-4472, 1992.

Jacobsen et al., "Novel 21-Aminosteroids That Inhibit Iron-Dependent Lipid Peroxidation and Protect against Central Nervous System Trauma," *J. Med. Chem.* 33(4): 1145-1151, 1990.

Jeffcoat and James, *New Comprehensive Biochemistry* vol. 7: *Fatty Acid Metabolism and Its Regulation*, Elsevier Science Publishers B.V., Amsterdam, The Netherlands, Chapter 4, "The regulation of desaturation and elongation of fatty acids in mammals," 85-112, 1984.

Kim et al., "ARC POMC mRNA and PVN α-MSH are lower in obese relative to lean Zucker rats," *Brain Research* 862: 11-16, 2000.

Kurtz et al., "The Zucker Fatty Rat as a Genetic Model of Obesity and Hypertension," *Hypertension* 13(6, Part 2): 896-901, Jun. 1989.

Lee et al., "β-Cell lipotoxicity in the pathogenesis of non-insulin-dependent diabetes mellitus of obese rats: Impairment in adipocyte-β-cell relationships," *Proc. Natl. Acad. Sci. USA* 91: 10878-10882, Nov. 1994.

Lefevre et al., "Effects of Polyunsaturated Fatty Acids and Clofibrate on Chicken Stearoyl-CoA Desaturase 1 Gene Expression," *Biochemical and Biophysical Research Communications* 280(1): 25-31, 2001.

Lin et al., "CNS melanocortin and leptin effects on stearoyl-CoA desaturase-1 and resistin expression," *Biochemical and Biophysical Research Communications* 311: 324-328, 2003.

Miyazaki et al, "The Biosynthesis of Hepatic Cholesterol Esters and Triglycerides is Impaired in Mice with a Disruption of the Gene for Stearoyl-CoA Desaturase 1," *The Journal of Biological Chemistry* 275(39): 30132-30138, Sep. 29, 2000.

Miyazaki et al., "A lipogenic diet in mice with a disruption of the stearoyl-CoA desaturase 1 gene reveals a stringent requirement of endogenous monounsaturated fatty acids for triglyceride synthesis," *J. Lipid Res.* 42: 1018-1024, 2001.

Miyazaki et al., "Targeted Disruption of Stearoyl-CoA Desaturase1 Gene in Mice Causes Atrophy of Sebaceous and Meibomian Glands and Depletion of Wax Esters in the Eyelid," *J. Nutrition* 131: 2260-2268, 2001.

Ntambi et al., "Loss of stearoyl-CoA desaturase-1 function protects mice against adiposity," *Proc. Natl. Acad. Sci. USA* 99(17): 11482-11486, Aug. 20, 2002.

Ntambi, "Regulation of stearoyl-CoA desaturase by polyunsaturated fatty acids and cholesterol," *Journal of Lipid Research* 40: 1549-1558, 1999.

Park et al., "Lipid Level and Type Alter Stearoyl CoA Desaturase mRNA Abundance Differently in Mice with Distinct Susceptibilities to Diet-Influenced Diseases," *J. Nutrition* 566-573, 1997.

Ratouis et al., "Synthesis and Pharmacological Study of New Piperazine Derivatives. II. Phenethylpiperazines," *Journal of Medicinal Chemistry* 8: 104-107, Jan. 1965.

Rowley et al., "4-Heterocyclylpiperidines as Selective High-Affinity Ligands at the Human Dopamine D4 Receptor," *J. Med. Chem.* 40(15): 2374-2385, 1997.

Simopoulos, "Essential fatty acids in health and chronic disease," *Am. J. Clin. Nutr.* 70(suppl): 560S-569S, 1999.

Sjögren et al., "Fatty acid desaturases in human adipose tissue: relationships between gene expression, desaturation indexes and insulin resistance," *Diabetologia* 51: 328-335, 2008.

Steck and Fletcher, "Pyridazines. VII. Some 3-Dialkylaminopyridazines (1)," *Journal of Heterocyc. Chem.* 11: 1077-1079, Dec. 1974.

Toldy et al., "Piperazinderivate I. 3,4,5-Trimethoxybenzoylderivate, Eine Neue Verbindungsgruppe mit Antiulzerogener Wirkung," *Acta Chimica Academiae Scientiarum Hungaricae* 49(3): 265-286, 1966.

Truett et al., "Rat obesity gene fatty (fa) maps to chromosome 5: Evidence for homology with the mouse gene diabetes (db)," *Proc. Natl. Acad. Sci USA* 88: 7806-7809, Sep. 1991.

Vice et al., "Concise Formation of 4-Benzyl Piperidines and Related Derivatives Using a Suzuki Protocol," *J. Org. Chem.* 66: 2487-2492, 2001.

Warensjö et al., "Polymorphisms in the *SCD1* Gene: Associations With Body Fat Distribution and Insulin Sensitivity," *Obesity* 15(7): 1732-1740, Jul. 2007.

Wolfe et al., "Simple, Efficient Catalyst System for the Palladium-Catalyzed Amination of Aryl Chlorides, Bromides, and Triflates," *J. Org. Chem.* 65(4): 1158-1174, 2000.

Xin et al., "Discovery of piperidine-aryl urea-based stearoyl-CoA desaturase 1 inhibitors," *Bioorganic & Medicinal Chemistry Letters* 18: 4298-4302, 2008.

Zhang et al., "Down-regulation of the Expression of the Obese Gene by an Antidiabetic Thiazolidinedione in Zucker Diabetic Fatty Rats and db/db Mice," *The Journal of Biological Chemistry* 271(16): 9455-9459, Apr. 19, 1996.

Zheng et al., "*Scd1* is expressed in sebaceous glands and is disrupted in the asebia mouse," *Nature Genetics* 23: 268-270, Nov. 1999.

CAS Registry No. 504430-63-1, Apr. 24, 2003, 2 pages.
CAS Registry No. 362000-30-4, Oct. 14, 2001, 2 pages.
Medline PMID No. 596247, 1977, 1 page.
EMBASE No. 1978142387, 2006, 1 page.
BIOSIS No. 198069026634, 1979, 1 page.
CAPLUS on STN, Accession No. 1967:473577, 1967, 3 pages.
CAPLUS on STN, Accession No. 1968:95776, 1968, 3 pages.
CAPLUS on STN, Accession No. 1977:601475, 1977, 5 pages.
CAPLUS Accession No. 1997: 218911, Registry No. 126:291605, 1997, 1 page.
CAPLUS on STN, Accession No. 1994:54512, 1993, 3 pages.

CAPLUS on STN, Accession No. 1985:185052, 1984, 3 pages.
Advisory Action dated May 25, 2006 from U.S. Appl. No. 10/326,210, filed Dec. 20, 2002.
Advisory Action dated Jul. 31, 2007 from U.S. Appl. No. 10/326,210, filed Dec. 20, 2002.
Advisory Action dated Sep. 27, 2007 from U.S. Appl. No. 10/326,210, filed Dec. 20, 2002.
Office Action dated Jun. 6, 2008 from U.S. Appl. No. 11/575,640, filed Mar. 20, 2007.
Office Action dated Jan. 10, 2006 from U.S. Appl. No. 10/326,210, filed Dec. 20, 2002.
Office Action dated Jan. 14, 2009 from U.S. Appl. No. 10/885,901, filed Jul. 6, 2004.
Office Action dated Feb. 12, 2007 from U.S. Appl. No. 10/885,901, filed Jul. 6, 2004.
Office Action dated Apr. 19, 2007 from U.S. Appl. No. 10/326,210, filed Dec. 20, 2002.
Office Action dated May 20, 2005 from U.S. Appl. No. 10/326,210, filed Dec. 20, 2002.
Office Action dated Jun. 4, 2008 from U.S. Appl. No. 10/885,901, filed Jul. 6, 2004.
Office Action dated Sep. 17, 2007 from U.S. Appl. No. 10/885,901, filed Jul. 6, 2004.
Office Action dated Sep. 26, 2008 from U.S. Appl. No. 11/575,638, filed Mar. 20, 2007.
Office Action dated Oct. 25, 2006 from U.S. Appl. No. 10/326,210, filed Dec. 20, 2002.
Office Action dated May 30, 2008 from U.S. Appl. No. 11/575,643, filed Mar. 20, 2007.
Office Action dated Nov. 25, 2008 from U.S. Appl. No. 11/575,641, filed Nov. 2, 2007.
Office Action dated Jan. 27, 2009 from U.S. Appl. No. 11/575,640, filed Mar. 20, 2007.
Office Action dated May 26, 2009 from U.S. Appl. No. 11/575,645, filed Sep. 25, 2007.
Office Action dated Jul. 7, 2009 from U.S. Appl. No. 11/575,638, filed Mar. 20, 2007.
Office Action dated Jul. 10, 2009 from U.S. Appl. No. 11/575,642, filed Oct. 3, 2007.
Office Action dated Sep. 2, 2009 from U.S. Appl. No. 11/575,640, filed Mar. 20, 2007.
Abuzar et al., "Synthesis of 2-Carbalkoxyamino-5(6)-(1-substituted piperazin-4-yl/piperazin-4-ylcarbonyl)benzimidazoles and Related Compounds as Potential Anthelmintics," *Pharmazie* 39(H. 11): 747-749, 1984.
Castro, "Pyridazine derivatives XII. Synthesis and antipsychotic-antidepressant activity of some butyrophenone derivatives of 6-phenylpyridazine," *Eur. J. Med. Chem.* 29: 831-839, 1994.
Dobrzyn and Ntambi, "Stearoyl-CoA desaturase: A Therapeutic target of insulin resistance and diabetes," *Drug Discovery Today: Therapeutic Strategies* 2(2): 125-128, 2005.
Durrington et al., Embase No. 1978142387, 1978, 1 page; see also Durrington et al., "The effect of a low-cholesterol, high-polyunsaturate diet on serum lipid levels, apolipoprotein B levels and triglyceride fatty acid composition," *Atherosclerosis* 27: 465-475, 1977.
Ghibaudi et al., "Fat Intake Affects Adiposity, Comorbidity Factors, and Energy Metabolism of Sprague-Dawley Rats," *Obesity Research* 10(9): 956-963, Sep. 2002.
Grundy et al., "Diagnosis and Management of the Metabolic Syndrome: An American Heart Association/National Heart, Lung, and Blood Institute—Scientific Statement—Executive Summary," *Cardiology in Review* 13(6): 322-327, Nov./Dec. 2005.
Ivanov et al., CAPLUS, Accession No. 137339-85-6, 1991, 1 page; see also Ivanov et al., "Spectral Properties of Bisbenzimidasoles Interacting with Nucleic Acids," *Bioorganicheskaya Khimiya* 17(8): 1041-1047, 1991.
Jeffcoat et al., "Stearoyl-CoA Desaturase: A Control Enzyme in Hepatic Lipogenesis," *Eur. J. Biochem* 101: 439-445, 1979.
Kirkeby et al., Medline PMID No. 596247, 1977, 1 page; see also, Kirkeby et al., "Effects of Prolonged, Strenuous Exercise on Lipids and Thyroxine in Serum," *Acta Med. Scand.* 202: 463-467, 1977.

Kumar et al., "Possible Anthelmintic Agents : Syntheses of Ethyl 5(6)-[5(6)-Substituted-2-benzimidazolyl]benzimidazole-2-carbamates & Ethyl 4,6-Dinitro-5-substituted-amino-benzimidazole-2-carbamates," *Indian J. Chem.* 20B: 254-256, Mar. 1981.
Kuznetsov et al., Caplus Accession No. 111861-11-1, 1987, 1 page; see also, Kuznetsov et al., "Derivatives of 5(6)-Aminobenzimidazole," *Zhurnal Organicheskoi Khimii* 23(3): 637-642, Mar. 1987.
Latt and Stetten, "Spectral Studies on 33258 Hoechst and Related Bisbenzimidazole Dyes Useful for Fluorescent Detection of Deoxyribonucleic Acid Synthesis," *The Journal of Histochemistry and Cytochemistry* 24(1): 24-33, 1976.
Loewe and Urbanietz, CAPLUS Accession No. 23470-26-0, 1974, 3 pages; see also, Loewe and Urbanietz, "Basic substituted 2,6-bisbenzimidazole derivatives, a novel series of substances with chemotherapeutic activity," *Arzneimittel-Forschung* 24(12): 1927-1933, 1974.
Luo et al., CAPLUS Accession No. 1999:55733, Registry No. 130:332501, 1999, 1 page.
Ohashi, Biosis No. 198069026634, 1980, 1 page; see also, Ohashi, "Changes in cholesterol content and fatty acid composition of serum lipid in irradiated rat," *Okayama Igakkai Zasshi* 91(1-2): 241-249, 1979.
Ohkubo et al., "Studies on Cerebral Protective Agents. VIII. Synthesis of 2-Aminothiazoles and 2-Thiazolecarboxamides with Antianoxic Activity," *Chem. Pharm. Bull.* 43(9): 1497-1504, 1995.
Okamoto et al., "Novel ORL1-selective antagonists with oral bioavailability and brain penetrability," *Bioorganic & Medicinal Chemistry Letters* 18: 3282-3285, 2008.
Pan and Sun, "Soluble Polymer-Supported Synthesis of Arylpiperazines," *Tetrahedron Letters* 39: 9505-9508, 1998.
Patel and Rybczynski, "Treatment of non-insulin-dependent diabetes mellitus," *Expert Opin. Investig. Drugs* 12(4): 623-633, 2003.
Ravina et al., Abstract Database CAPLUS on STN, Accession No. 1994:54512, 1994, 3 pages; see also Ravina et al., "Synthesis and Potential Anthelmintic Activity of Methyl-5-(4-salicyloyl-piperazin-1-yl)-benzimidazole-2-carbamates," *Arzneim.-Forsch./Drug Res.* 43(I-6): 689-694, 1993.
Sánchez-Alonso et al., "Piperazine derivatives of benzimidazole as potential anthelmintics," *Pharmazie* 44(9): 606-607, 1989.
Shanklin and Somerville, "Stearoyl-acyl-carrier-protein desaturase from higher plants is structurally unrelated to the animal and fungal homologs," *Proc. Natl. Acad. Sci. USA* 88: 2510-2514, Mar. 1991.
Shanklin et al., "Eight Histidine Residues Are Catalytically Essential in a Membrane-Associated Iron Enzyme, Stearoyl-CoA Desaturase, and Are Conserved in Alkane Hydroxylase and Xylene Monooxygenase," *Biochemistry* 33(43): 12787-12794, 1994.
Singh and Ram., "New Local Anaesthetics," *The Indian Journal of Pharmacy* 34(3): 74-76, Mar. 1972.
Stoehr and Vogt-Schaden, CAPLUS Accession No. 23617-78-9, 1981, 1 page; see also, Stöhr and Vogt-Schaden, "A New Dual Staining Technique for Simultaneous Flow Cytometric DNA Analysis of Living and Dead Cells," *Flow Cytometry IV* 274: 96-99, 1980.
Talamo and Bloch, "A New Assay for Fatty Acid Desaturation," *Analytical Biochemistry* 29: 300-304, 1969.
Thunus, CAPLUS on STN, Accession No. 1977:601475, 1977, 5 pages; see also, "Synthèse et propriétés pharmacologiques de quelques isopropyl et hydroxyéthylpipérazinylpyridines (substitution 2,5)," *Annales pharmaceutiques françaises* 35(5-6): 197-203, 1977.
Toldy et al., CAPLUS on STN, Accession No. 1967:473577, 1967, 3 pages; see also, Toldy et al., Piperazinderivative, II: Chlorobenzoxamin-Analoga, *Acta Chimica Acad. Sci. Hung. Tomus* 52(3): 283-299, 1967.
Toldy et al., CAPLUS on STN, Accession No. 1968:95776, 1968, 3 pages; see also, Toldy et al., "Phenthiazinderivate, VII: Versuche zur darstellung von selektiv wirkenden phenthiazinderivaten," *Acta Chimica Academiae Scientiarum Hungaricae Tomus* 53(3): 279-294, 1967.

White and Martin, CAPLUS Accession No. 1997:218911, 1997, 1 page; see also, White and Martin, "Evidence for a Central Mechanism of Obesity in the Zucker Rat: Role of Neuropeptide Y and Leptin," *P.S.E.B.M. 214*: 222-232, 1997.

Wityak et al., "Discovery and Initial SAR of 2-Amino-5-carboxamidothiazoles as Inhibitors of the Src-family Kinase p56$^{Lck}$," *Bioorg. Med. Chem. Lett. 13*: 4007-4010, 2003.

Contreras et al., "Aminopyridazines as Acetylcholinesterase Inhibitors," *J. Med. Chem.* 42(4): 730-741, 1999.

Isabel et al., "Biological activity and preclinical efficacy of azetidinyl pyridazines as potent systemically-distributed stearoyl-CoA desaturase inhibitors," *Bioorganic & Medicinal Chemistry Letters 21*: 479-483, 2011.

Liu, "Stearoyl-CoA desaturase inhibitors: update on patented compounds," *Expert Opin. Ther. Patents* 19(9): 1169-1191, 2009.

Liu et al., "Discovery of Potent, Selective, Orally Bioavailable Stearoyl-CoA Desaturase 1 Inhibitors," *J. Med. Chem.* 50(13): 3086-3100, 2007.

Robert et al., "Synthesis and antileishmanil activity of new imidazolidin-2-one derivatives," *European Journal of Medicinal Chemistry 38*: 711-718, 2003.

Tucker et al., "Piperazinyl Oxazolidinone Antibacterial Agents Containing a Pyridine, Diazene, or Triazene Heteroaromatic Ring," *J. Med. Chem.* 41(19): 3727-3735, 1998.

SUBSTITUTED PYRIDAZINES AS STEAROYL-CoA DESATURASE INHIBITORS

FIELD OF THE INVENTION

The present invention relates generally to the field of inhibitors of stearoyl-CoA desaturase, such as heterocyclic derivatives, and uses for such compounds in treating and/or preventing various human diseases, including those mediated by stearoyl-CoA desaturase (SCD) enzymes, preferably SCD1, especially diseases related to elevated lipid levels, cardiovascular disease, diabetes, obesity, metabolic syndrome and the like.

BACKGROUND OF THE INVENTION

Acyl desaturase enzymes catalyze the formation of double bonds in fatty acids derived from either dietary sources or de novo synthesis in the liver. Mammals synthesize at least three fatty acid desaturases of differing chain length specificity that catalyze the addition of double bonds at the delta-9, delta-6, and delta-5 positions. Stearoyl-CoA desaturases (SCDs) introduce a double bond in the C9-C10 position of saturated fatty acids. The preferred substrates are palmitoyl-CoA (16:0) and stearoyl-CoA (18:0), which are converted to palmitoleoyl-CoA (16:1) and oleoyl-CoA (18:1), respectively. The resulting mono-unsaturated fatty acids are substrates for incorporation into phospholipids, triglycerides, and cholesteryl esters.

A number of mammalian SCD genes have been cloned. For example, two genes have been cloned from rat (SCD1, SCD2) and four SCD genes have been isolated from mouse (SCD1, 2, 3, and 4). While the basic biochemical role of SCD has been known in rats and mice since the 1970's (Jeffcoat, R. et al., *Elsevier Science* (1984), Vol. 4, pp. 85-112; de Antueno, R J, *Lipids* (1993), Vol. 28, No. 4, pp. 285-290), it has only recently been directly implicated in human disease processes.

A single SCD gene, SCD1, has been characterized in humans. SCD1 is described in Brownlie et al, PCT published patent application, WO 01/62954, the disclosure of which is hereby incorporated by reference in its entirety. A second human SCD isoform has recently been identified, and because it bears little sequence homology to alternate mouse or rat isoforms it has been named human SCD5 or hSCD5 (PCT published patent application, WO 02/26944, incorporated herein by reference in its entirety).

To date, no small-molecule, drug-like compounds are known that specifically inhibit or modulate SCD activity. Certain long-chain hydrocarbons have been used historically to study SCD activity. Known examples include thia-fatty acids, cyclopropenoid fatty acids, and certain conjugated linoleic acid isomers. Specifically, cis-12, trans-10 conjugated linoleic acid is believed to inhibit SCD enzyme activity and reduce the abundance of SCD1 mRNA while cis-9, trans-11 conjugated linoleic acid does not. Cyclopropenoid fatty acids, such as those found in sterculia and cotton seeds, are also known to inhibit SCD activity. For example, sterculic acid (8-(2-octylcyclopropenyl)octanoic acid) and malvalic acid (7-(2-octylcyclopropenyl)heptanoic acid) are C18 and C16 derivatives of sterculoyl and malvaloyl fatty acids, respectively, having cyclopropene rings at their C9-C10 position. These agents are believed to inhibit SCD enzymatic activity by direct interaction with the enzyme, thus inhibiting delta-9 desaturation. Other agents that may inhibit SCD activity include thia-fatty acids, such as 9-thiastearic acid (also called 8-nonylthiooctanoic acid) and other fatty acids with a sulfoxy moiety.

These known modulators of delta-9 desaturase activity are not useful for treating the diseases and disorders linked to SCD1 biological activity. None of the known SCD inhibitor compounds are selective for SCD or delta-9 desaturases, as they also inhibit other desaturases and enzymes. The thia-fatty acids, conjugated linoleic acids and cyclopropene fatty acids (malvalic acid and sterculic acid) are neither useful at reasonable physiological doses, nor are they specific inhibitors of SCD1 biological activity, rather they demonstrate cross inhibition of other desaturases, in particular the delta-5 and delta-6 desaturases by the cyclopropene fatty acids.

The absence of small molecule inhibitors of SCD enzyme activity is a major scientific and medical disappointment because evidence is now compelling that SCD activity is directly implicated in common human disease processes: See e.g., Attie, A. D. et al., "Relationship between stearoyl-CoA desaturase activity and plasma triglycerides in human and mouse hypertriglyceridemia", *J. Lipid Res.* (2002), Vol. 43, No. 11, pp. 1899-907; Cohen, P. et al., "Role for stearoyl-CoA desaturase-1 in leptin-mediated weight loss", *Science* (2002), Vol. 297, No. 5579, pp. 240-3, Ntambi, J. M. et al., "Loss of stearoyl-CoA desaturase-1 function protects mice against adiposity", *Proc. Natl. Acad. Sci. USA*. (2002), Vol. 99, No. 7, pp. 11482-6.

The present invention solves this problem by presenting new classes of compounds that are useful in modulating SCD activity and regulating lipid levels, especially plasma lipid levels, and which are useful in the treatment of SCD-mediated diseases such as diseases related to dyslipidemia and disorders of lipid metabolism, especially diseases related to elevated lipid levels, cardiovascular disease, diabetes, obesity, metabolic syndrome and the like.

BRIEF SUMMARY OF THE INVENTION

The present invention provides heterocyclic derivatives that modulate the activity of stearoyl-CoA desaturase. Methods of using such derivatives to modulate the activity of stearoyl-CoA desaturase and pharmaceutical compositions comprising such derivatives are also encompassed.

Accordingly, in one aspect, the invention provides compounds of formula (I):

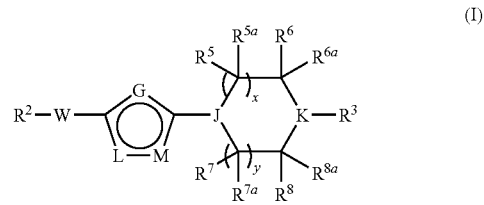

wherein:

x and y are each independently 0, 1, 2 or 3;

G is —N($R^4$)—, —O—, —S(O)$_t$— (where t is 0, 1 or 2), —C($R^4$)= or —C($R^4$)=C($R^4$)—;

J and K are each independently N or C($R^{10}$);

L and M are each independently —N=, —N($R^4$)—, or —C($R^4$)=, provided that when G is —C($R^4$)= or —C($R^4$)=C($R^4$)—, L and M can not both be —C($R^4$)=;

W is a direct bond, —N($R^1$)C(O)—, —C(O)N($R^1$)—, —OC(O)N($R^1$)—, —N($R^1$)C(O)N($R^1$)—, —O—, —N($R^1$)—, —S(O)$_t$— (where t is 0, 1 or 2), —N($R^1$)S(O)$_p$— (where p is 1 or 2), —S(O)$_p$N($R^1$)— (where p is 1 or 2), —C(O)—, —OS(O)$_2$N(R$^1$)—, —OC(O)—, —C(O)O—, or —N(R$^1$)C(O)O—;

each R$^1$ is independently selected from the group consisting of hydrogen, C$_1$-C$_{12}$alkyl, C$_2$-C$_{12}$hydroxyalkyl, C$_4$-C$_{12}$cycloalkylalkyl and C$_7$-C$_{19}$aralkyl;

R$^2$ is selected from the group consisting of C$_1$-C$_{12}$alkyl, C$_2$-C$_{12}$alkenyl, C$_2$-C$_{12}$hydroxyalkyl, C$_2$-C$_{12}$hydroxyalkenyl, C$_2$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$heterocyclyl, C$_3$-C$_{12}$heterocyclylalkyl, C$_1$-C$_{12}$heteroaryl, and C$_3$-C$_{12}$heteroarylalkyl;

or R$^2$ is a multi-ring structure having 2 to 4 rings wherein the rings are independently selected from the group consisting of cycloalkyl, heterocyclyl, aryl and heteroaryl and where some or all of the rings may be fused to each other;

R$^3$ is selected from the group consisting of hydrogen, C$_1$-C$_{12}$alkyl, C$_2$-C$_{12}$alkenyl, C$_2$-C$_{12}$hydroxyalkyl, C$_2$-C$_{12}$hydroxyalkenyl, C$_2$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$heterocyclyl, C$_3$-C$_{12}$heterocyclylalkyl, C$_1$-C$_{12}$heteroaryl and C$_3$-C$_{12}$heteroarylalkyl;

or R$^3$ is a multi-ring structure having 2 to 4 rings wherein the rings are independently selected from the group consisting of cycloalkyl, heterocyclyl, aryl and heteroaryl and where some or all of the rings may be fused to each other;

each R$^4$ is independently selected from hydrogen, fluoro, chloro, C$_1$-C$_{12}$alkyl, C$_1$-C$_{12}$alkoxy, haloalkyl, cyano, nitro or —N(R$^9$)$_2$;

or two adjacent R$^4$ groups, together with the carbons to which they are attached, may form an aryl, heteroaryl or heterocyclyl ring system;

R$^5$, R$^{5a}$, R$^6$, R$^{6a}$, R$^7$, R$^{7a}$, R$^8$ and R$^{8a}$ are each independently selected from hydrogen or C$_1$-C$_3$alkyl;

or R$^5$ and R$^{5a}$ together, R$^6$ and R$^{6a}$ together, or R$^7$ and R$^{7a}$ together, or R$^8$ and R$^{8a}$ together are an oxo group;

or one of R$^5$, R$^{5a}$, R$^6$ and R$^{6a}$ together with one of R$^7$, R$^{7a}$, R$^8$ and R$^{8a}$ forms a direct bond or an alkylene bridge, while the remaining R$^5$, R$^{5a}$, R$^6$, R$^{6a}$, R$^7$, R$^{7a}$, R$^8$, and R$^{8a}$ are each independently selected from hydrogen or C$_1$-C$_3$alkyl;

each R$^9$ is independently selected from hydrogen or C$_1$-C$_6$alkyl; and

R$^{10}$ is independently selected from hydrogen, fluoro, chloro, C$_1$-C$_{12}$alkyl or C$_1$-C$_{12}$alkoxy.

a stereoisomer, enantiomer or tautomer thereof, a pharmaceutically acceptable salt thereof, a pharmaceutical composition thereof or a prodrug thereof.

It is understood that the scope of the invention relating to the compounds of formula (I) as described above is not intended to encompass compounds specifically disclosed and/or claimed in previous publications, including, but not limited to, the compounds specifically disclosed in the following publications:

PCT Published Patent Application, WO 03/076400;
PCT Published Patent Application, WO 03/066604;
PCT Published Patent Application, WO 01/019822;
PCT Published Patent Application, WO 99/021834;
PCT Published Patent Application, WO 99/020606;
PCT Published Patent Application, WO 98/001446;
PCT Published Patent Application, WO 94/012495;
European Published Patent Application, 0 300 526;
European Published Patent Application, 0 156 433;
European Published Patent Application, 0 055 583;
European Published Patent Application, 0 009 655;
U.S. Pat. No. 5,719,154; and
U.S. Pat. No. 5,494,908.

In another aspect, the invention provides methods of treating an SCD-mediated disease or condition in a mammal, preferably a human, wherein the methods comprise administering to the mammal in need thereof a therapeutically effective amount of a compound of the invention as set forth above.

In another aspect, the invention provides compounds or pharmaceutical compositions useful in treating, preventing and/or diagnosing a disease or condition relating to SCD biological activity such as the diseases encompassed by cardiovascular disorders and/or metabolic syndrome (including dyslipidemia, insulin resistance and obesity).

In another aspect, the invention provides methods of preventing or treating a disease or condition related to elevated lipid levels, such as plasma lipid levels, especially elevated triglyceride or cholesterol levels, in a patient afflicted with such elevated levels, comprising administering to said patient a therapeutically or prophylactically effective amount of a composition as disclosed herein. The present invention also relates to novel compounds having therapeutic ability to reduce lipid levels in an animal, especially triglyceride and cholesterol levels.

In another aspect, the invention provides pharmaceutical compositions comprising the compounds of the invention as set forth above, and pharmaceutically acceptable excipients. In one embodiment, the present invention relates to a pharmaceutical composition comprising a compound of the invention in a pharmaceutically acceptable carrier and in an amount effective to modulate triglyceride level, or to treat diseases related to dyslipidemia and disorders of lipid metabolism, when administered to an animal, preferably a mammal, most preferably a human patient. In an embodiment of such composition, the patient has an elevated lipid level, such as elevated plasma triglycerides or cholesterol, before administration of said compound and said compound is present in an amount effective to reduce said lipid level.

In another aspect, the invention provides methods for treating a patient for, or protecting a patient from developing, a disease or condition mediated by stearoyl-CoA desaturase (SCD), which methods comprise administering to a patient afflicted with such disease or condition, or at risk of developing such disease or condition, a therapeutically effective amount of a compound that inhibits activity of SCD in a patient when administered thereto.

In another aspect, the invention provides methods for treating a range of diseases involving lipid metabolism utilizing compounds identified by the methods disclosed herein. In accordance therewith, there is disclosed herein a range of compounds having said activity, based on a screening assay for identifying, from a library of test compounds, a therapeutic agent which modulates the biological activity of said SCD and is useful in treating a human disorder or condition relating to serum levels of lipids, such as triglycerides, VLDL, HDL, LDL, and/or total cholesterol.

DETAILED DESCRIPTION OF THE INVENTION

Definitions

Certain chemical groups named herein are preceded by a shorthand notation indicating the total number of carbon atoms that are to be found in the indicated chemical group. For example; C$_7$-C$_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

Accordingly, as used in the specification and appended claims, unless specified to the contrary, the following terms have the meaning indicated:

"Methoxy" refers to the —$OCH_3$ radical.

"Cyano" refers to the —CN radical.

"Nitro" refers to the —$NO_2$ radical.

"Trifluoromethyl" refers to the —$CF_3$ radical.

"Oxo" refers to the =O substituent.

"Thioxo" refers to the =S substituent.

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, an alkyl group may be optionally substituted by one of the following groups: alkyl, alkenyl, halo, haloalkenyl, cyano, nitro, aryl, cycloalkyl, heterocyclyl, heteroaryl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})(S(O)_tR^{16})$ (where t is 1 to 2), —$S(O)_tOR^{16}$ (where t is 1 to 2), —$S(O)_tR^{16}$ (where t is 0 to 2), and —$S(O)_tN(R^{14})_2$ (where t is 1 to 2) where each $R^{14}$ is independently hydrogen, alkyl, haloalkyl, cycloalkyl, cycloalkylalkyl, aryl (optionally substituted with one or more groups selected from halo or haloalkyl), aralkyl, heterocyclyl, heterocyclylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise indicated.

"$C_1$-$C_3$alkyl" refers to an alkyl radical as defined above containing one to three carbon atoms. The $C_1$-$C_3$alkyl radical may be optionally substituted as defined for an alkyl group.

"$C_1$-$C_6$alkyl" refers to an alkyl radical as defined above containing one to six carbon atoms. The $C_1$-$C_6$alkyl radical may be optionally substituted as defined for an alkyl group.

"$C_1$-$C_{12}$alkyl" refers to an alkyl radical as defined above containing one to twelve carbon atoms. The $C_1$-$C_{12}$alkyl radical may be optionally substituted as defined for an alkyl group.

"$C_2$-$C_6$alkyl" refers to an alkyl radical as defined above containing two to six carbon atoms. The $C_2$-$C_6$alkyl radical may be optionally substituted as defined for an alkyl group.

"$C_3$-$C_6$alkyl" refers to an alkyl radical as defined above containing three to six carbon atoms. The $C_3$-$C_6$alkyl radical may be optionally substituted as defined for an alkyl group.

"$C_3$-$C_{12}$alkyl" refers to an alkyl radical as defined above containing three to twelve carbon atoms. The $C_3$-$C_{12}$alkyl radical may be optionally substituted as defined for an alkyl group.

"$C_6$-$C_{12}$alkyl" refers to an alkyl radical as defined above containing six to twelve carbon atoms. The $C_6$-$C_{12}$alkyl radical may be optionally substituted as defined for an alkyl group.

"$C_7$-$C_{12}$alkyl" refers to an alkyl radical as defined above containing seven to twelve carbon atoms. The $C_7$-$C_{12}$alkyl radical may be optionally substituted as defined for an alkyl group.

"Alkenyl" refers to a straight or branched hydrocarbon chain radical group consisting solely of carbon and hydrogen atoms, containing at least one double bond, having from two to twelve carbon atoms, preferably one to eight carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one of the following groups: alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})(S(O)_t R^{16})$ (where t is 1 to 2), —$S(O)_tOR^{16}$ (where t is 1 to 2), —$S(O)_tR^{16}$ (where t is 0 to 2), and —$S(O)_tN(R^{14})_2$ (where t is 1 to 2) where each $R^{14}$ is independently hydrogen, alkyl, haloalkyl, cycloalkyl, cycloalkylalkyl, aryl, haloalkyl, heterocyclyl, heterocyclylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_3$-$C_{12}$alkenyl" refers to an alkenyl radical as defined above containing three to 12 carbon atoms. The $C_3$-$C_{12}$alkenyl radical may be optionally substituted as defined for an alkenyl group.

"$C_2$-$C_{12}$alkenyl" refers to an alkenyl radical as defined above containing two to 12 carbon atoms. The $C_2$-$C_{12}$alkenyl radical may be optionally substituted as defined above for an alkenyl group.

"Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, preferably having from one to eight carbons, e.g., methylene, ethylene, propylene, n-butylene, and the like. The alkylene chain may be attached to the rest of the molecule and to the radical group through one carbon within the chain or through any two carbons within the chain. The alkylene chain may be optionally substituted by one of the following groups: alkyl, alkenyl, halo, haloalkenyl, cyano, nitro, aryl, cycloalkyl, heterocyclyl, heteroaryl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})(S(O)_tR^{16})$ (where t is 1 to 2), —$S(O)_tOR^{16}$ (where t is 1 to 2), —$S(O)_tR^{16}$ (where t is 0 to 2), and —$S(O)_tN(R^{14})_2$ (where t is 1 to 2) where each $R^{14}$ is independently hydrogen, alkyl, haloalkyl, cycloalkyl, cycloalkylalkyl, aryl (optionally substituted with one or more groups selected from halo or haloalkyl), aralkyl, heterocyclyl, heterocyclylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise indicated.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. The alkenylene chain may be optionally substituted by one of the following groups: alkyl, alkenyl, halo, haloalkenyl, cyano, nitro, aryl, cycloalkyl, heterocyclyl, heteroaryl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)(S(O)$_t$R$^{16}$) (where t is 1 to 2), —S(O)$_t$OR$^{16}$ (where t is 1 to 2), —S(O)$_t$R$^{16}$ (where t is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl (optionally substituted with one or more groups selected from halo or haloalkyl), aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise indicated.

"Alkylene bridge" refers to a straight or branched divalent hydrocarbon bridge, linking two different carbons of the same ring structure, consisting solely of carbon and hydrogen, containing no unsaturation and having from one to twelve carbon atoms, preferably having from one to eight carbons, e.g., methylene, ethylene, propylene, n-butylene, and the like. The alkylene bridge may link any two carbons within the ring structure.

"Alkoxy" refers to a radical of the formula —OR$_a$ where R$_a$ is an alkyl radical as defined above. The alkyl part of the alkoxy radical may be optionally substituted as defined above for an alkyl radical.

"$C_1$-$C_6$alkoxy" refers to an alkoxy radical as defined above containing one to six carbon atoms. The alkyl part of the $C_1$-$C_6$alkoxy radical may be optionally substituted as defined above for an alkyl group.

"$C_1$-$C_{12}$alkoxy" refers to an alkoxy radical as defined above containing one to twelve carbon atoms. The alkyl part of the $C_1$-$C_{12}$alkoxy radical may be optionally substituted as defined above for an alkyl group.

"$C_3$-$C_{12}$alkoxy" refers to an alkoxy radical as defined above containing three to twelve carbon atoms. The alkyl part of the $C_3$-$C_{12}$alkoxy radical may be optionally substituted as defined above for an alkyl group.

"Alkoxyalkyl" refers to a radical of the formula —R$_a$—O—R$_a$ where each R$_a$ is independently an alkyl radical as defined above. The oxygen atom may be bonded to any carbon in either alkyl radical. Each alkyl part of the alkoxyalkyl radical may be optionally substituted as defined above for an alkyl group.

"$C_2$-$C_{12}$alkoxyalkyl" refers to an alkoxyalkyl radical as defined above containing two to twelve carbon atoms. Each alkyl part of the $C_2$-$C_{12}$alkoxyalkyl radical may be optionally substituted as defined above for an alkyl group.

"$C_3$alkoxyalkyl" refers to an alkoxyalkyl radical as defined above containing three carbon atoms. Each alkyl part of the $C_3$alkoxyalkyl radical may be optionally substituted as defined above for an alkyl group.

"$C_3$-$C_{12}$alkoxyalkyl" refers to an alkoxyalkyl radical as defined above containing three to twelve carbon atoms. Each alkyl part of the $C_3$-$C_{12}$alkoxyalkyl radical may be optionally substituted as defined above for an alkyl group.

"Alkylsulfonyl" refers to a radical of the formula —S(O)$_2$R$_a$ where R$_a$ is an alkyl group as defined above. The alkyl part of the alkylsulfonyl radical may be optionally substituted as defined above for an alkyl group.

"$C_1$-$C_6$alkylsulfonyl" refers to an alkylsulfonyl radical as defined above having one to six carbon atoms. The $C_1$-$C_6$alkylsulfonyl group may be optionally substituted as defined above for an alkylsulfonyl group.

"Aryl" refers to aromatic monocyclic or multicyclic hydrocarbon ring system consisting only of hydrogen and carbon and containing from 6 to 19 carbon atoms, preferably 6 to 10 carbon atoms, where the ring system may be partially or fully saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, —R$^{15}$—N(R$^{14}$)C(O)OR$^{16}$, —R$^{15}$—N(R$^{14}$)C(O)R$^{16}$, —R$^{15}$—N(R$^{14}$)(S(O)$_t$R$^{16}$) (where t is 1 to 2), —R$^{15}$—S(O)$_t$OR$^{16}$ (where t is 1 to 2), —R$^{15}$—S(O)$_t$R$^{16}$ (where t is 0 to 2), and —R$^{15}$—S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each R$^{15}$ is independently a direct bond or a straight or branched alkylene or alkenylene chain; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"Aralkyl" refers to a radical of the formula —R$_a$R$_b$ where R$_a$ is an alkyl radical as defined above and R$_b$ is one or more aryl radicals as defined above, e.g., benzyl, diphenylmethyl and the like. The aryl part of the aralkyl radical may be optionally substituted as described above for an aryl group. The alkyl part of the aralkyl radical may be optionally substituted as defined above for an alkyl group.

"$C_7$-$C_{12}$aralkyl" refers to an aralkyl group as defined above containing seven to twelve carbon atoms. The aryl part of the $C_7$-$C_{12}$aralkyl radical may be optionally substituted as described above for an aryl group. The alkyl part of the $C_7$-$C_{12}$aralkyl radical may be optionally substituted as defined above for an alkyl group.

"$C_7$-$C_{19}$aralkyl" refers to an aralkyl group as defined above containing seven to nineteen carbon atoms. The aryl part of the $C_7$-$C_{19}$aralkyl radical may be optionally substituted as described above for an aryl group. The alkyl part of the $C_7$-$C_{19}$aralkyl radical may be optionally substituted as defined above for an alkyl group.

"$C_{13}$-$C_{19}$aralkyl" refers to an aralkyl group as defined above containing thirteen to nineteen carbon atoms. The aryl part of the $C_{13}$-$C_{19}$aralkyl radical may be optionally substituted as described above for an aryl group. The alkyl part of the $C_{13}$-$C_{19}$aralkyl radical may be optionally substituted as defined above for an alkyl group.

"Aralkenyl" refers to a radical of the formula —R$_c$R$_b$ where R$_c$ is an alkenyl radical as defined above and R$_b$ is one or more aryl radicals as defined above, which may be optionally substituted as described above. The aryl part of the aralkenyl radical may be optionally substituted as described above for an aryl group. The alkenyl part of the aralkenyl radical may be optionally substituted as defined above for an alkenyl group.

"Aryloxy" refers to a radical of the formula —OR$_b$ where R$_b$ is an aryl group as defined above. The aryl part of the aryloxy radical may be optionally substituted as defined above.

"Aryl-$C_1$-$C_6$alkyl" refers to a radical of the formula —R$_h$—R$_i$ where R$_h$ is an unbranched alkyl radical having one to six carbons and R$_i$ is an aryl group attached to the terminal carbon of the alkyl radical.

"Cycloalkyl" refers to a stable non-aromatic monocyclic or bicyclic hydrocarbon radical consisting solely of carbon and hydrogen atoms, having from three to fifteen carbon atoms, preferably having from three to twelve carbon atoms, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})(S(O)_tR^{16})$ (where t is 1 to 2), $-R^{15}-S(O)_tOR^{16}$ (where t is 1 to 2), $-R^{15}-S(O)_tR^{16}$ (where t is 0 to 2), and $-R^{15}-S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_3$-$C_6$cycloalkyl" refers to a cycloalkyl radical as defined above having three to six carbon atoms. The $C_3$-$C_6$cycloalkyl radical may be optionally substituted as defined above for a cycloalkyl group.

"$C_3$-$C_{12}$cycloalkyl" refers to a cycloalkyl radical as defined above having three to twelve carbon atoms. The $C_3$-$C_{12}$cycloalkyl radical may be optionally substituted as defined above for a cycloalkyl group.

"Cycloalkylalkyl" refers to a radical of the formula $-R_aR_d$ where $R_a$ is an alkyl radical as defined above and $R_d$ is a cycloalkyl radical as defined above. The cycloalkyl part of the cycloalkyl radical may be optionally substituted as defined above for an cycloalkyl radical. The alkyl part of the cycloalkyl radical may be optionally substituted as defined above for an alkyl radical.

"$C_4$-$C_{12}$cycloalkylalkyl" refers to a cycloalkylalkyl radical as defined above having four to twelve carbon atoms. The $C_4$-$C_{12}$cycloalkylalkyl radical may be optionally substituted as defined above for a cycloalkylalkyl group.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above, e.g., 2-bromoethenyl, 3-bromoprop-1-enyl, and the like. The alkenyl part of the haloalkenyl radical may be optionally substituted as defined above for an alkyl group.

"Heterocyclyl" refers to a stable 3- to 18-membered non-aromatic ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, $-R^{15}-OR^{14}$, $-R^{15}-C(O)-R^{14}$, $-R^{15}-N(R^{14})_2$, $-R^5-C(O)R^{14}$, $-R^{15}-C(O)OR^{14}$, $-R^{15}-C(O)N(R^{14})_2$, $-R^{15}-N(R^{14})C(O)R^{16}$, $-R^{15}-N(R^{14})C(O)R^{16}$, $-R^{15}-N(R^{14})(S(O)_tR^{16})$ (where t is 1 to 2), $-R^{15}-S(O)_tOR^{16}$ (where t is 1 to 2), $-R^{15}-S(O)_tR^{16}$ (where t is 0 to 2), and $-R^{15}-S(O)_tN(R^{14})_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_3$-$C_{12}$heterocyclyl" refers to a heterocyclyl radical as defined above having three to twelve carbons. The $C_3$-$C_{12}$heterocyclyl may be optionally substituted as defined above for a heterocyclyl group.

"Heterocyclylalkyl" refers to a radical of the formula $-R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"$C_3$-$C_{12}$heterocyclylalkyl" refers to a heterocyclylalkyl radical as defined above having three to twelve carbons. The $C_3$-$C_{12}$heterocyclylalkyl radical may be optionally substituted as defined above for a heterocyclylalkyl group.

"Heteroaryl" refers to a 5- to 18-membered aromatic ring radical which consists of carbon atoms and from one to five heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—OC(O)—$R^{14}$—$R^{15}$—N($R^{14}$)$_2$, —$R^{15}$—C(O)$R^{14}$, —$R^{15}$—C(O)$R^{14}$, —$R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)(S(O)$_t R^{16}$) (where t is 1 to 2), —$R^{15}$—S(O)$_t OR^{16}$ (where t is 1 to 2), —$R^{15}$—S(O)$_t R^{16}$ (where t is 0 to 2), and —$R^{15}$—S(O)$_t$N($R^{14}$)$_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_1$-$C_{12}$heteroaryl" refers to a heteroaryl radical as defined above having one to twelve carbon atoms. The $C_1$-$C_{12}$heteroaryl group may be optionally substituted as defined above for a heteroaryl group.

"$C_5$-$C_{12}$heteroaryl" refers to a heteroaryl radical as defined above having five to twelve carbon atoms. The $C_5$-$C_{12}$heteroaryl group may be optionally substituted as defined above for a heteroaryl group.

"Heteroarylalkyl" refers to a radical of the formula —$R_a R_f$ where $R_a$ is an alkyl radical as defined above and $R_f$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"$C_3$-$C_{12}$heteroarylalkyl" refers to a heteroarylalkyl radical as defined above having three to twelve carbon atoms. The $C_3$-$C_{12}$heteroarylalkyl group may be optionally substituted as defined above for a heteroarylalkyl group.

"Heteroarylcycloalkyl" refers to a radical of the formula —$R_d R_f$ where $R_d$ is a cycloalkyl radical as defined above and $R_f$ is a heteroaryl radical as defined above. The cycloalkyl part of the heteroarylcycloalkyl radical may be optionally substituted as defined above for a cycloalkyl group. The heteroaryl part of the heteroarylcycloalkyl radical may be optionally substituted as defined above for a heteroaryl group.

"Heteroarylalkenyl" refers to a radical of the formula —$R_b R_f$ where $R_b$ is an alkenyl radical as defined above and $R_f$ is a heteroaryl radical as defined above. The heteroaryl part of the heteroarylalkenyl radical may be optionally substituted as defined above for a heteroaryl group. The alkenyl part of the heteroarylalkenyl radical may be optionally substituted as defined above for an alkenyl group.

"Hydroxyalkyl" refers to a radical of the formula —$R_a$—OH where $R_a$ is an alkyl radical as defined above. The hydroxy group may be attached to the alkyl radical on any carbon within the alkyl radical. The alkyl part of the hydroxyalkyl group may be optionally substituted as defined above for an alkyl group.

"$C_2$-$C_{12}$hydroxyalkyl" refers to a hydroxyalkyl radical as defined above containing two to twelve carbon atoms. The alkyl part of the $C_2$-$C_{12}$hydroxyalkyl radical may be optionally substituted as defined above for an alkyl group.

"$C_3$-$C_{12}$hydroxyalkyl" refers to a hydroxyalkyl radical as defined above containing three to twelve carbon atoms. The alkyl part of the $C_3$-$C_{12}$hydroxyalkyl radical may be optionally substituted as defined above for an alkyl group.

"$C_7$-$C_{12}$hydroxyalkyl" refers to a hydroxyalkyl radical as defined above containing seven to twelve carbon atoms. The alkyl part of the $C_7$-$C_{12}$hydroxyalkyl radical may be optionally substituted as defined above for an alkyl group.

"Hydroxyalkenyl" refers to a radical of the formula —$R_c$—OH where $R_c$ is an alkenyl radical as defined above. The hydroxy group may be attached to the alkenyl radical on any carbon within the alkenyl radical. The alkenyl part of the hydroxyalkenyl group may be optionally substituted as defined above for an alkenyl group.

"$C_2$-$C_{12}$hydroxyalkenyl" refers to a hydroxyalkenyl radical as defined above containing two to twelve carbon atoms. The alkenyl part of the $C_2$-$C_{12}$hydroxyalkenyl radical may be optionally substituted as defined above for an alkenyl group.

"$C_3$-$C_{12}$hydroxyalkenyl" refers to a hydroxyalkenyl radical as defined above containing three to twelve carbon atoms. The alkenyl part of the $C_3$-$C_{12}$hydroxyalkenyl radical may be optionally substituted as defined above for an alkenyl group.

"Hydroxyl-$C_1$-$C_6$-alkyl" refers to a radical of the formula —$R_h$—OH where $R_h$ is an unbranched alkyl radical having one to six carbons and the hydroxy radical is attached to the terminal carbon.

"Trihaloalkyl" refers to an alkyl radical, as defined above, that is substituted by three halo radicals, as defined above, e.g., trifluoromethyl. The alkyl part of the trihaloalkyl radical may be optionally substituted as defined above for an alkyl group.

"$C_1$-$C_6$-trihaloalkyl" refers to a trihaloalkyl radical as defined above having one to six carbon atoms. The $C_1$-$C_6$trihaloalkyl may be optionally substituted as defined above for a trihaloalkyl group.

"Trihaloalkoxy" refers to a radical of the formula —$OR_g$ where $R_g$ is a trihaloalkyl group as defined above. The trihaloalkyl part of the trihaloalkoxy group may be optionally substituted as defined above for a trihaloalkyl group.

"$C_1$-$C_6$trihaloalkoxy" refers to a trihaloalkoxy radical as defined above having one to six carbon atoms. The $C_1$-$C_6$trihaloalkoxy group may be optionally substituted as defined above for a trihaloalkoxy group.

"A multi-ring structure" refers to a multicyclic ring system comprised of two to four rings wherein the rings are independently selected from cycloalkyl, aryl, heterocyclyl or heteroaryl as defined above. Each cycloalkyl may be optionally substituted as defined above for a cycloalkyl group. Each aryl may be optionally substituted as defined above for an aryl group. Each heterocyclyl may be optionally substituted as defined above for a heterocyclyl group. Each heteroaryl may be optionally substituted as defined above for a heteroaryl group. The rings may be attached to other through direct bonds or some or all of the rings may be fused to each other. Examples include, but are not limited to a cycloalkyl radical substituted by aryl group; a cycloalkyl group substituted by an aryl group, which, in turn, is substituted by another aryl group; and so forth.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of an SCD-mediated disease or condition in the mammal, preferably a human. The amount of a compound of the invention which constitutes a "therapeutically effective amount" will vary depending on the compound, the condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development; or (iii) relieving the disease or condition, i.e., causing regression of the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The chemical naming protocol and structure diagrams used herein employ and rely the chemical naming features as utilized by Chemdraw version 7.0.1 (available from Cambridgesoft Corp., Cambridge, Mass.). For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms which are assumed to be bonded to sufficient hydrogen atoms to complete the valency.

For example, a compound of formula (I) wherein x and y are both 1; G is —C(H)=C(H)—; J and K are both N; L and M are both —N=; W is —N(H)C(O)—; $R^2$ is 2-cyclopropylethyl and $R^3$ is 5-trifluoromethylpyridin-2-yl, i.e., a compound of the following formula:

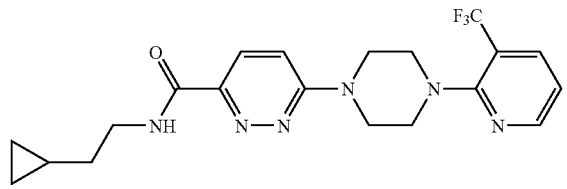

is named herein as 6-[4-(3-trifluoromethylpyridin-2-yl)piperazin-1-yl]pyridazine-3-carboxylic acid (2-cyclopropylethyl)amide.

Certain radical groups of the compounds of the invention are depicted herein as linkages between two parts of the compounds of the invention. For example, in the following formula (I):

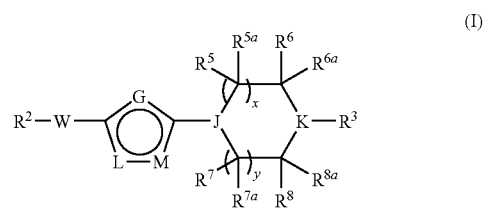

W is described, for example, as being —N($R^1$)C(O)—, —C(O)N($R^1$)—, or —N($R^1$)C(O)N($R^1$)—. This description is meant to describe a W group attached to the $R^2$ group as follows: $R^2$—N($R^1$)C(O)—, $R^2$—C(O)N($R^1$)—, or $R^2$—N($R^1$)C(O)N($R^1$)—. In other words, the description of the W linkage groups are meant to be read from left to right in view of formula (I) as depicted above.

Embodiments of the Invention

Of the compounds of formula (I) disclosed above in the Summary of the Invention, one embodiment are those compounds where J and K are both N, i.e., compounds having the following formula (Ia):

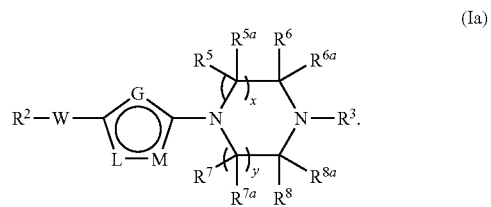

Of this embodiment, one embodiment are the compounds of formula (Ia) wherein:

x and y are each 1;

G is —C($R^4$)=C($R^4$)—;

L and M are both —N=;

W is —N($R^1$)C(O)—, —C(O)N($R^1$)—, —OC(O)N($R^1$)—, —N($R^1$)C(O)N($R^1$)—, —N($R^1$)S(O)$_p$— (where p is 1 or 2), —S(O)$_p$N($R^1$)— (where p is 1 or 2), —OS(O)$_2$N($R^1$)—, —C(O)O— or —N($R^1$)C(O)O—;

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_7$-$C_{12}$alkyl, $C_2$-$C_{12}$alkenyl, $C_7$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_{13}$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

$R^3$ is selected from the group consisting of aryl, $C_3$-$C_{12}$heterocyclyl and $C_1$-$C_{12}$heteroaryl; and each $R^4$ is independently selected from hydrogen, fluoro, chloro, $C_1$-$C_{12}$alkyl, $C_1$-$C_{12}$alkoxy, haloalkyl, cyano, nitro or —N($R^9$)$_2$;

$R^5$, $R^{5a}$, $R^6$, $R^{6a}$, $R^7$, $R^{7a}$, $R^8$ and $R^{8a}$ are each independently selected from hydrogen or $C_1$-$C_3$alkyl;

provided that $R^2$ is not $C_5$-$C_{10}$pyrazinylalkyl, pyridinonyl, pyrrolidinonyl, methylimidazolyl or phenyl substituted with amino.

Of this embodiment, one embodiment are those compounds where $R^3$ is aryl.

Specific embodiments of this embodiment include, but are not limited to, the compounds selected from the group consisting of:
6-[4-(4-Fluorophenyl)-piperazin-1-yl]-pyridazine-3-carboxylic acid (2-cyclopropylethyl)amide; and
6-[4-(3-Trifluoromethylphenyl)-piperazin-1-yl]pyridazine-3-carboxylic acid (2-cyclopropylethyl)amide.

Of this embodiment, another embodiment are those compounds where $R^3$ is $C_1$-$C_{12}$heteroaryl.

Specific embodiments of this embodiment include, but are not limited to, the compounds selected from the group consisting of:
6-(4-Benzooxazol-2-yl-piperazin-1-yl)pyridazine-3-carboxylic acid (2-cyclopropylethyl)amide;
6-(4-Benzothiazol-2-yl-piperazin-1-yl)-pyridazine-3-carboxylic acid (2-cyclopropylethyl)amide;
6-(4-Quinazolin-4-yl-piperazin-1-yl)-pyridazine-3-carboxylic acid (2-cyclopropylethyl)amide;
6-[4-(3-Trifluoromethylpyridin-2-yl)piperazin-1-yl]pyridazine-3-carboxylic acid (2-cyclopropylethyl)amide;
6-(4-Benzo[d]isothiazol-3-yl-piperazin-1-yl)pyridazine-3-carboxylic acid (2-cyclopropylethyl)amide;
6-(4-Pyridin-2-yl-piperazin-1-yl)pyridazine-3-carboxylic acid (2-cyclopropylethyl)amide; and
6-[4-(3-Oxo-3H-isoindol-1-yl)piperazin-1-yl]pyridazine-3-carboxylic acid (2-cyclopropylethyl)amide.

In another embodiment of the invention, the compounds of formula (I) do not include the following "excluded" compounds, as designated by their Chemical Abstract Registry Nos. ("RN"), as defined by the Chemical Abstract Service of the American Chemical Society (Washington, D.C.):
RN 331242-58-1;
RN 202135-24-8;
RN 202135-25-9;
RN 202135-26-0;
RN 202135-27-1;
RN 202135-28-2;
RN 202135-36-2;
RN 100241-46-1;
RN 100241-62-1;
RN 100224-53-1;
RN 100224-54-2;
RN 100224-67-7;
RN 100241-07-4;
RN 100241-08-5;
RN 100241-46-1;
RN 100241-52-9;
RN 100241-53-0;
RN 100241-54-1;
RN 100241-55-2;
RN 83773-90-4; and
RN 75842-08-9.

In yet another embodiment of the invention, a group of compounds of formula (I) is directed to compounds where x and y are each 1; J and K are each independently N; G is —C($R^4$)=C($R^4$)—; L and M are both —N=; W is direct bond; $R^2$ is $C_1$-$C_4$alkyl; $R^3$ is substituted phenyl, with the proviso $R^3$ is substituted with substituents other than fluoro and substituted oxazolidine.

In yet another embodiment of the invention, a group of compounds of formula (I) is directed to compounds where x is 1, 2 or 3 and y is 1; J is N or C($R^{10}$) and K is N; G is —C($R^4$)=C($R^4$)—; L and M are each independently —N= or —C($R^4$)=, provided that L and M can not both be —C($R^4$)=; W is —N($R^1$)C(O)—, —C(O)N($R^1$)—, or —C(O)—; $R^3$ is selected from $C_1$-$C_{12}$alkyl, aryl, $C_1$-$C_{12}$heteroaryl, $C_3$-$C_{12}$cycloalkyl, $C_3$-$C_{12}$heterocyclyl, multi-ring structure having 2 to 4 rings wherein the rings are independently selected from the group consisting of cycloalkyl, heterocyclyl, aryl and heteroaryl and where some or all of the rings may be fused to each other; with the proviso that $R^2$ is other than $C_{1-6}$ alkyl, $C_{1-6}$ alkyloxy, and aryl$C_{1-6}$ alkyl.

In yet another embodiment of the invention, a group of compounds of formula (I) is directed to compounds where G is —N($R^4$)— or —C($R^4$)=, L is —N($R^4$)— and M is —N($R^4$)— or —C($R^4$)=.

Specific embodiments of the above-described embodiments of the invention are disclosed herein in the Examples set forth below.

In another embodiment of the invention, the methods of the invention are directed towards the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, cardiovascular disease, diabetes, obesity, metabolic syndrome and the like by administering an effective amount of a compound of the invention.

The present invention also relates to pharmaceutical composition containing the compounds of the invention. In one embodiment, the invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

Utility and Testing of the Compounds of the Invention

The present invention relates to compounds, pharmaceutical compositions and methods of using the compounds and pharmaceutical compositions for the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, especially cardiovascular disease, diabetes, obesity, metabolic syndrome and the like, by administering to a patient in need of such treatment an effective amount of an SCD-modulating, especially inhibiting, agent.

In general, the present invention provides a method for treating a patient for, or protecting a patient from developing, a disease related to dyslipidemia and/or a disorder of lipid metabolism, wherein lipid levels in an animal, especially a human being, are outside the normal range (i.e., abnormal lipid level, such as elevated plasma lipid levels), especially levels higher than normal, preferably where said lipid is a fatty acid, such as a free or complexed fatty acid, triglycerides, phospholipids, or cholesterol, such as where LDL-cholesterol levels are elevated or HDL-cholesterol levels are reduced, or any combination of these, where said lipid-related condition or disease is an SCD-mediated disease or condition, comprising administering to an animal, such as a mammal, especially a human patient, a therapeutically effective amount of a compound of the invention or a pharmaceutical composition comprising a compound of the invention wherein the compound modulates the activity of SCD, preferably human SCD1.

The compounds of the invention modulate, preferably inhibit, the activity of human SCD enzymes, especially human SCD1.

The general value of the compounds of the invention in modulating, especially inhibiting, the activity of SCD can be determined using the assay described below in Example 4. Alternatively, the general value of the compounds in treating disorders and diseases may be established in industry standard animal models for demonstrating the efficacy of compounds in treating obesity, diabetes or elevated triglyceride or cholesterol levels or for improving glucose tolerance. Such models include Zucker obese fa/fa rats (available from Harlan Sprague Dawley, Inc. (Indianapolis, Ind.)), or the Zucker diabetic fatty rat (ZDF/GmiCrl-fa/fa) (available from Charles River Laboratories (Montréal, Quebec)).

The compounds of the instant invention are inhibitors of delta-9 desaturases and are useful for treating diseases and disorders in humans and other organisms, including all those human diseases and disorders which are the result of aberrant delta-9 desaturase biological activity or which may be ameliorated by modulation of delta-9 desaturase biological activity.

As defined herein, an SCD-mediated disease or condition includes but is not limited to a disease or condition which is, or is related to, cardiovascular disease, dyslipidemias (including but not limited to disorders of serum levels of triglycerides, hypertriglyceridemia, VLDL, HDL, LDL, fatty acid Desaturation Index (e.g. the ratio of 18:1/18:0 fatty acids, or other fatty acids, as defined elsewhere herein), cholesterol, and total cholesterol, hypercholesterolemia, as well as cholesterol disorders (including disorders characterized by defective reverse cholesterol transport), familial combined hyperlipidemia, coronary artery disease, atherosclerosis, heart disease, cerebrovascular disease (including but not limited to stroke, ischemic stroke and transient ischemic attack (TIA)), peripheral vascular disease, and ischemic retinopathy. In a preferred embodiment, compounds of the invention will, in a patient, increase HDL levels and/or decrease triglyceride levels and/or decrease LDL or non-HDL-cholesterol levels.

An SCD-mediated disease or condition also includes metabolic syndrome (including but not limited to dyslipidemia, obesity and insulin resistance, hypertension, microalbuminemia, hyperuricaemia, and hypercoagulability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cachexia and anorexia), weight loss, body mass index and leptin related diseases. In a preferred embodiment, compounds of the invention will be used to treat diabetes mellitus and obesity.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaemia, hypercoagulability and/or microalbuminemia.

An SCD-mediated disease or condition also includes fatty liver, hepatic steatosis, hepatitis, non-alcoholic hepatitis, non-alcoholic steatohepatitis (NASH), alcoholic hepatitis, acute fatty liver, fatty liver of pregnancy, drug-induced hepatitis, erythrohepatic protoporphyria, iron overload disorders, hereditary hemochromatosis, hepatic fibrosis, hepatic cirrhosis, hepatoma and conditions related thereto.

An SCD-mediated disease or condition also includes but is not limited to a disease or condition which is, or is related to primary hypertriglyceridemia, or hypertriglyceridemia secondary to another disorder or disease, such as hyperlipoproteinemias, familial histiocytic reticulosis, lipoprotein lipase deficiency, apolipoprotein deficiency (such as ApoCII deficiency or ApoE deficiency), and the like, or hypertriglyceridemia of unknown or unspecified etiology.

An SCD-mediated disease or condition also includes a disorder of polyunsaturated fatty acid (PUFA) disorder, or a skin disorder, including but not limited to eczema, acne, psoriasis, keloid scar formation or prevention, diseases related to production or secretions from mucous membranes, such as monounsaturated fatty acids, wax esters, and the like.

An SCD-mediated disease or condition also includes inflammation, sinusitis, asthma, pancreatitis, osteoarthritis, rheumatoid arthritis, cystic fibrosis, and pre-menstrual syndrome.

An SCD-mediated disease or condition also includes but is not limited to a disease or condition which is, or is related to cancer, neoplasia, malignancy, metastases, tumours (benign or malignant), carcinogenesis, hepatomas and the like.

An SCD-mediated disease or condition also includes a condition where increasing lean body mass or lean muscle mass is desired, such as is desirable in enhancing performance through muscle building. Myopathies and lipid myopathies such as carnitine palmitoyltransferase deficiency (CPT I or CPT II) are also included herein. Such treatments are useful in humans and in animal husbandry, including for administration to bovine, porcine or avian domestic animals or any other animal to reduce triglyceride production and/or provide leaner meat products and/or healthier animals.

An SCD-mediated disease or condition also includes a disease or condition which is, or is related to, neurological diseases, psychiatric disorders, multiple sclerosis, eye diseases, and immune disorders.

An SCD-mediated disease or condition also includes a disease or condition which is, or is related to, viral diseases or infections including but not limited to all positive strand RNA viruses, coronaviruses, SARS virus, SARS-associated coronavirus, Togaviruses, Picornaviruses, Coxsackievirus, Yellow Fever virus, Flaviviridae, ALPHAVIRUS (TOGAVIRIDAE) including Rubella virus, Eastern equine encephalitis virus, Western equine encephalitis virus, Venezuelan equine encephalitis virus, Sindbis virus, Semliki forest virus, Chikungunya virus, O'nyong'nyong virus, Ross river virus, Mayaro virus, Alphaviruses; ASTROVIRIDAE including Astrovirus, Human Astroviruses; CALICIVIRIDAE including Vesicular exanthema of swine virus, Norwalk virus, Calicivirus, Bovine calicivirus, Pig calcivirus, Hepatitis E; CORONAVIRIDAE including Coronavirus, SARS virus, Avian infectious bronchitis virus, Bovine coronavirus, Canine coronavirus, Feline infectious peritonitis virus, Human coronavirus 299E, Human coronavirus OC43, Murine hepatitis virus, Porcine epidemic diarrhea virus, Porcine hemagglutinating encephalomyelitis virus, Porcine transmissible gastroenteritis virus, Rat coronavirus, Turkey coronavirus, Rabbit coronavirus, Berne virus, Breda virus;

FLAVIVIRIDAE including Hepatitis C virus, West Nile virus, Yellow Fever virus, St. Louis encephalitis virus, Dengue Group, Hepatitis G virus, Japanese B encephalitis virus, Murray Valley encephalitis virus, Central European tick-borne encephalitis virus, Far Eastern tick-borne encephalitis virus, Kyasanur forest virus, Louping ill virus, Powassan virus, Omsk hemorrhagic fever virus, Kumilinge virus, Absetarov anzalova hypr virus, Ilheus virus, Rocio encephalitis virus, Langat virus, Pestivirus, Bovine viral diarrhea, Hog cholera virus, Rio Bravo Group, Tyuleniy Group, Ntaya Group, Uganda S Group, Modoc Group; PICORNAVIRIDAE including Coxsackie A virus, Rhinovirus, Hepatitis A virus, Encephalomyocarditis virus, Mengovirus, ME virus, Human poliovirus 1, Coxsackie B; POTYVIRIDAE including Potyvirus, Rymovirus, Bymovirus. Additionally it can be a disease or infection caused by or linked to Hepatitis viruses, Hepatitis B virus, Hepatitis C virus, human immunodeficiency virus (HIV) and the like. Treatable viral infections include those where the virus employs an RNA intermediate as part of the replicative cycle (hepatitis or HIV); additionally it can be a disease or infection caused by or linked to RNA negative strand viruses such as influenza and parainfluenza viruses.

The compounds identified in the instant specification inhibit the desaturation of various fatty acids (such as the C9-C10 desaturation of stearoyl-CoA) which is accomplished by delta-9 desaturases, such as stearoyl-CoA desaturase 1 (SCD1). As such these compounds inhibit the formation of various fatty acids and downstream metabolites thereof. This may lead to an accumulation of stearoyl-CoA or palmitoyl-CoA and other upstream precursors of various fatty acids; which may possibly result in a negative feedback loop causing an overall change in fatty acid metabolism. Any of these consequences may ultimately be responsible for the overall therapeutic benefit provided by these compounds.

Typically, a successful SCD inhibitory therapeutic agent will meet some or all of the following criteria. Oral availability should be at or above 20%. Animal model efficacy is less than about 2 mg/Kg, 1 mg/Kg, or 0.5 mg/Kg and the target human dose is between 50 and 250 mg/70 Kg, although doses outside of this range may be acceptable. ("mg/Kg" means milligrams of compound per kilogram of body mass of the subject to whom it is being administered). The therapeutic index (or ratio of toxic dose to therapeutic dose) should be greater than 100. The potency (as expressed by $IC_{50}$ value) should be less than 10 μM, preferably below 1 μM and most preferably below 50 nM. The $IC_{50}$ ("Inhibitory Concentration—50%") is a measure of the amount of compound required to achieve 50% inhibition of SCD activity, over a specific time period, in an SCD biological activity assay. Any process for measuring the activity of SCD enzymes, preferably mouse or human SCD enzymes, may be utilized to assay the activity of the compounds useful in the methods of the invention in inhibiting said SCD activity. Compounds of the invention demonstrate an $IC_{50}$ in a 15 minute microsomal assay of preferably less than 10 μM, less than 5 μM, less than 2.5 μM, less than 1 μM, less than 750 nM, less than 500 nM, less than 250 nM, less than 100 nM, less than 50 nM, and most preferably less than 20 nM. The compound of the invention may show reversible inhibition (i.e., competitive inhibition) and preferably does not inhibit other iron binding proteins. The required dosage should preferably be no more than about once or twice a day or at meal times.

The identification of compounds of the invention as SCD inhibitors was readily accomplished using the SCD enzyme and microsomal assay procedure described in Brownlie et al, supra. When tested in this assay, compounds of the invention had less than 50% remaining SCD activity at 10 μM concentration of the test compound, preferably less than 40% remaining SCD activity at 10 μM concentration of the test compound, more preferably less than 30% remaining SCD activity at 10 μM concentration of the test compound, and even more preferably less than 20% remaining SCD activity at 10 μM concentration of the test compound, thereby demonstrating that the compounds of the invention are potent inhibitors of SCD activity.

These results provide the basis for analysis of the structure-activity relationship (SAR) between test compounds and SCD. Certain R groups tend to provide more potent inhibitory compounds. SAR analysis is one of the tools those skilled in the art may now employ to identify preferred embodiments of the compounds of the invention for use as therapeutic agents.

Other methods of testing the compounds disclosed herein are also readily available to those skilled in the art. Thus, in addition, said contacting may be accomplished in vivo. In one such embodiment, said contacting in step (a) is accomplished by administering said chemical agent to an animal afflicted with a triglyceride (TG)- or very low density lipoprotein (VLDL)-related disorder and subsequently detecting a change in plasma triglyceride level in said animal thereby identifying a therapeutic agent useful in treating a triglyceride (TG)- or very low density lipoprotein (VLDL)-related disorder. In such embodiment, the animal may be a human, such as a human patient afflicted with such a disorder and in need of treatment of said disorder.

In specific embodiments of such in vivo processes, said change in SCD1 activity in said animal is a decrease in activity, preferably wherein said SCD1 modulating agent does not substantially inhibit the biological activity of a delta-5 desaturase, delta-6 desaturase or fatty acid synthetase.

The model systems useful for compound evaluation may include, but are not limited to, the use of liver microsomes, such as from mice that have been maintained on a high carbohydrate diet, or from human donors, including persons suffering from obesity. Immortalized cell lines, such as HepG2 (from human liver), MCF-7 (from human breast cancer) and 3T3-L1 (from mouse adipocytes) may also be used. Primary cell lines, such as mouse primary hepatocytes, are also useful in testing the compounds of the invention. Where whole animals are used, mice used as a source of primary hepatocyte cells may also be used wherein the mice have been maintained on a high carbohydrate diet to increase SCD activity in mirocrosomes and/or to elevate plasma triglyceride levels (i.e., the 18:1/18:0 ratio); alternatively mice on a normal diet or mice with normal triglyceride levels may be used. Mouse models employing transgenic mice designed for hypertriglyceridemia are also available as is the mouse phenome database. Rabbits and hamsters are also useful as animal models, especially those expressing CETP (cholesteryl ester transfer protein).

Another suitable method for determining the in vivo efficacy of the compounds of the invention is to indirectly measure their impact on inhibition of SCD enzyme by measuring a subject's Desaturation Index after administration of the compound. "Desaturation Index" as employed in this specification means the ratio of the product over the substrate for the SCD enzyme as measured from a given tissue sample. This may be calculated using three different equations 18:1n-9/18:0 (oleic acid over stearic acid); 16:1n-7/16:0 (palmitoleic acid over palmitic acid); and/or 16:1n-7+18:1n-7/16:0 (measuring all reaction products of 16:0 desaturation over 16:0 substrate). Desaturation Index is primarily measured in liver or plasma triglycerides, but may also be measured in other selected lipid fractions from a variety of tissues. Desaturation Index, generally speaking, is a tool for plasma lipid profiling.

A number of human diseases and disorders are the result of aberrant SCD1 biological activity and may be ameliorated by modulation of SCD1 biological activity using the therapeutic agents of the invention.

Inhibition of SCD expression may also affect the fatty acid composition of membrane phospholipids, as well as production or levels of triglycerides and cholesterol esters. The fatty acid composition of phospholipids ultimately determines membrane fluidity, while the effects on the composition of triglycerides and cholesterol esters can affect lipoprotein metabolism and adiposity.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

Those skilled in the art know how to determine suitable doses of the compounds for use in treating the diseases and disorders contemplated herein. Therapeutic doses are generally identified through a dose ranging study in humans based on preliminary evidence derived from animal studies. Doses must be sufficient to result in a desired therapeutic benefit without causing unwanted side-effects for the patient. The preferred dosage range for an animal is 0.001 mg/Kg to 10,000 mg/Kg, including 0.5 mg/Kg, 1.0 mg/Kg and 2.0 mg/Kg, though doses outside this range may be acceptable. The dosing schedule may be once or twice per day, although more often or less often may be satisfactory.

Those skilled in the art are also familiar with determining administration methods (oral, intravenous, inhalation, subcutaneous, etc.), dosage forms, suitable pharmaceutical excipients and other matters relevant to the delivery of the compounds to a subject in need thereof.

In an alternative use of the invention, the compounds of the invention can be used in in vitro or in vivo studies as exemplary agents for comparative purposes to find other compounds also useful in treatment of, or protection from, the various diseases disclosed herein.

Preparation of the Compounds of the Invention

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are well-known to those skilled in the art and as described herein.

The use of protecting groups is described in detail in Green, T.W. and P.G.M. Wutz, *Protective Groups in Organic Synthesis* (1999), 3rd Ed., Wiley. The protecting group may also be a polymer resin such as a Wang resin or a 2-chlorotritylchloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following Reaction Schemes illustrate methods to make compounds of this invention. It is understood that one of those skilled in the art would be able to make these compounds by similar methods or by methods known to one skilled in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this invention. $R^1$, $R^2$, $R^3$, $R^4$, $R^5$, $R^{5a}$, $R^6$, $R^{6a}$, $R^7$, $R^{7a}$, $R^8$ and $R^{8a}$ are defined in the following Reaction Schemes as in the Specification unless specifically defined otherwise. PG represents a protecting group such as BOC, benzyl group and the like.

Compounds of the invention may also be prepared by one skilled in the art by methods similar to those described in the following publications:

PCT Published Patent Application, WO 03/076400;
PCT Published Patent Application, WO 03/066604;
PCT Published Patent Application, WO 01/019822;
PCT Published Patent Application, WO 99/021834;
PCT Published Patent Application, WO 99/020606;
PCT Published Patent Application, WO 98/001446;
PCT Published Patent Application, WO 94/012495;
European Published Patent Application, 0 300 526;

European Published Patent Application, 0 156 433;
European Published Patent Application, 0 055 583;
European Published Patent Application, 0 009 655;
U.S. Pat. No. 5,719,154; and
U.S. Pat. No. 5,494,908

In general, the compounds of formula (I) of this invention can be synthesized following the general procedure as described below in Reaction Scheme 1, where L and M are both —N=; G is —C(R⁴)=C(R⁴)— and W is —N(R¹)C(O)—. It is understood that other compounds of formula (I) where L, M, G and W are defined otherwise as set forth in the Summary of the Invention above may be prepared in similar manner.

The methylpyridazine compound 101 can be oxidized to a carboxylic acid 102 by using an oxidant such as, but not limited to, potassium dichromate in an acid such as, but not limited to, concentrated sulfuric acid. Amide 103 can be formed from carboxylic acid 102 by reaction with an appropriate amine in the presence of a base such as, but not limited to, diisopropylethylamine, 1-hydroxyl-1H-benzotriazole and 1-ethyl-3-(3-dimethylaminopropyl)carbodiimide in a solvent such as, but not limited to, dichloromethane. Alternatively, amide 103 can be prepared by reaction of the acyl chloride derivative of 102 with an appropriate amine. The reaction can be performed in the presence of a base such as, but not limited to, diisopropylethylamine in a solvent such as, but not limited

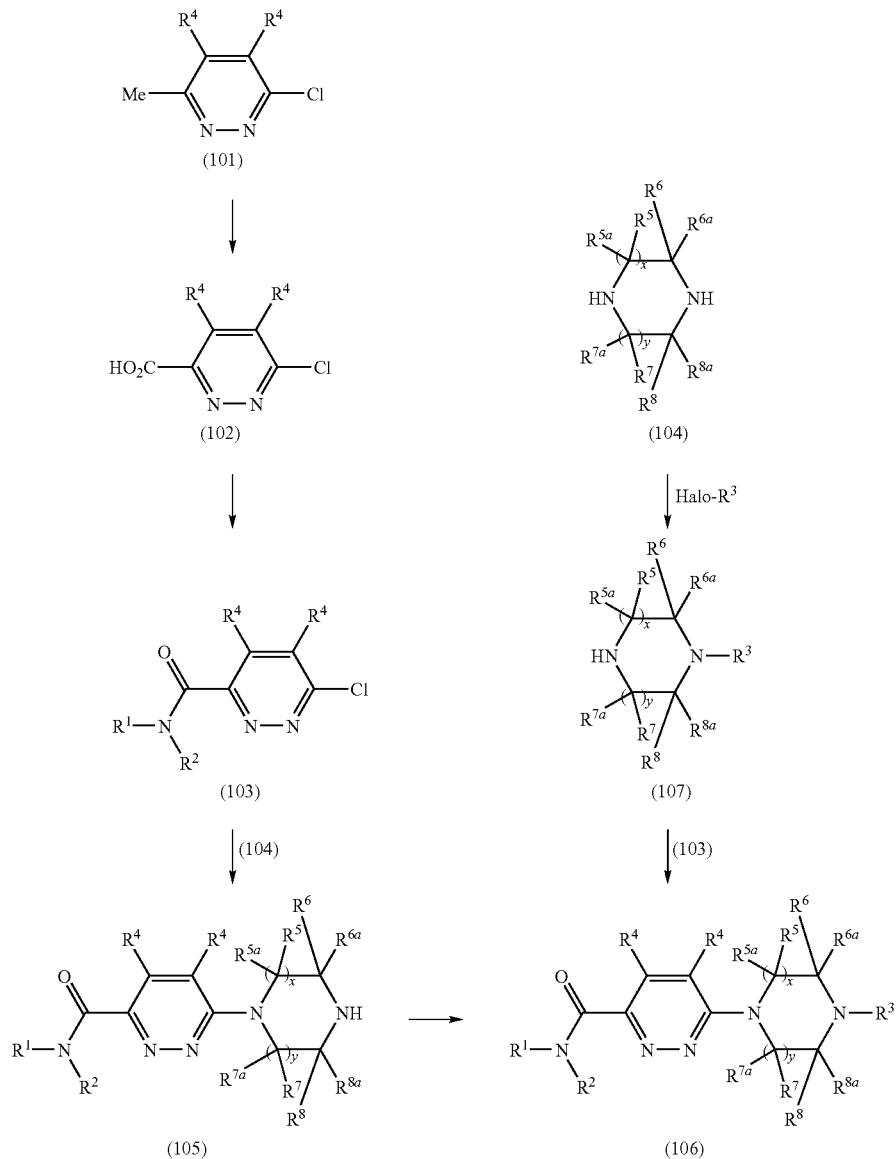

REACTION SCHEME 1

The starting materials for the above reaction scheme are commercially available or can be prepared according to methods known to one skilled in the art or by methods disclosed herein. In general, the compounds of the invention are prepared in the above reaction scheme as follows:

to, dichloromethane. Reaction of the chloropyridazine compound 103 with piperazine 104 in a refluxing acetonitrile gives compound 105. The final product 106 can be achieved by reacting the piperazine compound 105 with an heteroaromatic halide in the presence of 1,8-diazabicyclo[5,4,0]undec- 7-ene and catalytic amount of tetra-n-butylammonium iodide in a solvent such as, but not limited to, dioxane. Alternatively, compound 106 can be prepared by reaction of 105 with an appropriate arylhalide under Buchwald/Hartwig amination conditions (for example see Buchwald, S. L. et al J. Org. Chem. 2000, 65, 1158).

Alternatively, the piperazine compound 107 can be prepared from 104 by reacting 104 with a heteroaromatic halide or heteroaromatic amine under conditions known to one skilled in the art. Coupling of 107 with the chloropyridazine compound 103 in the presence of 1,8-diazabicyclo[5,4,0]undec-7-ene and catalytic amount of tetra-n-butylammonium iodide in a solvent such as, but not limited to, N,N-dimethylformamide gives the final product 106 as well.

Although anyone skilled in the art is capable of preparing the compounds of the invention according to the general techniques disclosed above, more specific details on synthetic techniques for compounds of the invention are provided elsewhere in this specification for convenience. Again, all reagents and reaction conditions employed in synthesis are known to those skilled in the art and are available from ordinary commercial sources.

Preparation 1

Synthesis of 3-Piperazin-1-Ylbenzo[D]Isothiazole

A mixture of anhydrous piperazine (2.75 g, 32 mmol) and 3-chloro-benzo[d]isothiazole (1.00 g, 5.80 mmol) were heated in a sealed tube in an oil bath at 125° C. for 24 hours. The orange melt was then quenched with ice water and 50% NaOH was added in one portion. The mixture was extracted with dichloromethane to get the crude product which was purified by recrystallization to afford the title compound as a pale yellow solid in 24% yield (0.260 g). MS (ES+) m/z 220 (M+1).

Preparation 2

Synthesis of 6-Chloropyridazine-3-Carboxylic Acid (2-Cyclopropylethyl)Amide

A. To a mechanically stirred solution of 3-chloro-6-methylpyridazine (155.6 mmol) in 140 mL of concentrated sulfuric acid, finely powdered potassium dichromate (55.40 g) was added slowly, the temperature being kept below 50° C. When the addition was complete, stirring was continued for another 4 hours at 50° C. The viscous, dark green liquid was then cooled and crushed ice was added cautiously. The reaction mixture was extracted with ethyl acetate (6×400 mL). The ethyl acetate extracts were combined, dried over anhydrous $Na_2SO_4$. The solvent was concentrated in vacuo to yield slightly red colored 6-chloropyridazine-3-carboxylic acid (106.6 mmol). This material was used for next reaction without further purification. Yield 69%. m.p. 145° C. (dec). $^1$H NMR (300 MHz, DMSO-$d_6$) δ 13.1, 8.20, 8.05.

B. To a solution of 6-chloropyridazine-3-carboxylic acid (15.8 mmol) in dichloromethane (95 mL) was added diisopropylethylamine (46.7 mmol), 1-hydroxybenzotriazole monohydrate (23.7 mmol) and 1-(3-dimethylaminopropyl)-3-ethylcarbodiimide (23.7 mmol) under nitrogen atmosphere at ambient temperature. The resulting mixture was stirred for 15 minutes and 2-cyclopropylethylamine (20.2 mmol) was added. After stirring for 36 hours at ambient temperature, the reaction mixture was diluted with dichloromethane (100 mL), then washed with water and dried over anhydrous $Na_2SO_4$. The solvent was removed in vacuo. Purification via column chromatography (30% ethyl acetate in hexanes) afforded the title compound (8.70 mmol). Yield 55%.

Preparation 3

Synthesis of 6-Piperazin-1-Ylpyridazine-3-Carboxylic Acid (2-Cyclopropylethyl)Amide A mixture of piperazine (1.48 g, 17.2 mmol) and 6-chloropyridazine-3-carboxylic acid (2-cyclopropylethyl)amide (1.29 g, 5.73 mmol) in acetonitrile (60 mL) was heated at reflux for 16 hours. After the reaction mixture was cooled, the gummy material was diluted with dichloromethane (50 mL), washed with water (2×20 mL), dried over $MgSO_4$. After filtration, the filtrate was concentrated in vacuo. The crude material was purified by column chromatography eluting with dichloromethane (100%) then with methanol:dichloromethane (1:9) to obtain 1.18 g (75%) of the product as a solid.

The syntheses of compounds of this invention are illustrated by, but not limited to the following examples.

EXAMPLE 1

Synthesis of 6-[4-(4-Fluorophenyl)Piperazin-1-Yl] Pyridazine-3-Carboxylic Acid (2-Cyclopropylethyl) Amide To a solution of 6-chloropyridazine-3-carboxylic acid (2-cyclopropylethyl)amide (0.120 g, 0.532 mmol) in DMF (2.3 mL) was treated with 1-(4-fluorophenyl)piperazine (0.117 g, 0.638 mmol) in the presence of 1,8-diazabicyclo[5,4,0]undec-7-ene (DBU) (0.23 mL, 1.54 mmol) and tetra-n-butylammonium iodide ($Bu_4NI$) (11 mg, 0.0298 mmol). The reaction mixture was heated at 75° C. to 80° C. for 15 hours, cooled to room temperature, diluted with ethyl acetate (100 mL). The organic layer was washed with water (3×10 mL), brine (3×10 mL), dried over $Na_2SO_4$, and then concentrated in vacuo. The crude product was purified by column chromatography to give the title compound as a white powder in 74% yield (0.146 g). $^1$H NMR (300 MHz, $CDCl_3$) δ 8.05-7.99 (m, 2H), 7.02-6.89 (m, 5H), 3.90 (t, J=5.2 Hz, 4H), 3.55 (m, 2H), 3.23 (t, J=5.2 Hz, 4H), 1.55-1.47 (m, 2H), 0.79-0.72 (m, 1H), 0.49-0.43 (m, 2H), 0.11-0.06 (m, 2H). MS (ES+) m/z 370.3 (M+1).

Example 1.1

Synthesis of 6-(4-Benzo[D]Isothiazol-3-Ylpiperazin-1-Yl)Pyridazine-3-Carboxylic Acid (2-Cyclopropylethyl)Amide Following the procedure as described in Example 1, making variation only as required to use 3-piperazin-1-ylbenzo[d]isothiazole to replace 1-(4-fluorophenyl)-piperazine to react with 6-chloropyridazine-3-carboxylic acid (2-cyclopropylethyl)amide, the title compound was obtained as a white powder in 25% yield (0.0307 g). $^1$H NMR (300 MHz, $CDCl_3$) δ 8.13 (d, J=9.5 Hz, 1H), 7.94 (m, 2H), 7.80 (d, J=8.0 Hz, 1H), 7.50 (t, J=7.3 Hz, 1H), 7.38 (t, J=7.8 Hz, 1H), 7.16 (d, J=8.0 Hz, 1H), 4.05 (m, 4H), 3.73 (m, 4H), 3.51 (m, 2H), 1.50 (m, 2H), 0.73 (m, 1H), 0.45 (m, 2H), 0.06 (m, 2H). MS (ES+) m/z 409 (M+1).

Example 1.2

Synthesis of 6-[4-(3-Trifluoromethylpyridin-2-Yl) Piperazin-1-Yl]Pyridazine-3-Carboxylic Acid (2-Cyclopropylethyl)Amide Following the procedure as described in Example 1, making variation only as required to use 1-(3-trifluoromethylpyridin-2-yl)piperazine to replace 1-(4-fluorophenyl)-piperazine to react with 6-chloropyridazine-3-carboxylic acid (2-cyclopropylethyl)amide, the title compound was obtained as a white powder in 43% yield (0.061 g). $^1$H NMR (300 MHz, CDCl$_3$) δ 8.44 (m, 1H), 8.01 (m, 2H), 7.89 (m, 1H), 7.02 (s, 2H), 3.88 (m, 4H), 3.54 (m, 2H), 3.41 (m, 4H), 1.51 (m, 2H), 0.78 (m, 1H), 0.45 (m, 2H), 0.07 (m, 2H). MS (ES+) m/z 421 (M+1).

Example 1.3

Synthesis of 6-(4-Pyridin-2-Ylpiperazin-1-Yl)Pyridazine-3-Carboxylic Acid (2-Cyclopropylethyl) Amide Following the procedure as described in Example 1, making variation only as required to use 1-pyridin-2-ylpiperazine to replace 1-(4-fluorophenyl)piperazine to react with 6-chloropyridazine-3-carboxylic acid (2-cyclopropylethyl)amide, the title compound was obtained as a white powder in 30% yield (0.036 g). $^1$H NMR (300 MHz, CDCl$_3$) δ 8.19 (m, 1H), 8.01 (m, 1H), 7.50 (m, 1H), 7.00 (d, J=9.9 Hz, 1H), 6.67 (m, 2H), 3.89 (m, 4H), 3.75 (m, 4H), 3.54 (m, 2H), 1.50 (m, 2H), 0.74 (m, 1H), 0.45 (m, 2H), 0.09 (m, 2H). $^{13}$C NMR (75 MHz, CDCl$_3$) δ 163.2, 160.2, 158.9, 147.9, 144.9, 137.8, 126.9, 113.8, 112.1, 107.2, 44.6, 39.6, 34.6, 8.67, 4.25. MS (ES+) m/z 353.6 (M+1).

Example 1.4

Synthesis of 6-[4-(3-Trifluoromethylphenyl)-Piperazin-1-Yl]-Pyridazine-3-Carboxylic Acid (2-Cyclopropylethyl)Amide Following the procedure as described in Example 1, making variation only as required to use 1-(3-trifluoromethylphenyl)piperazine to replace 1-(4-fluorophenyl)-piperazine to react with 6-chloropyridazine-3-carboxylic acid (2-cyclopropylethyl)amide, the title compound was obtained as a white powder in 57% yield (0.210 g). $^1$H NMR (300 MHz, CDCl$_3$) δ 8.09 (d, J=9.5 Hz, 1H), 7.98 (t, J=5.4 Hz, 1H), 7.38 (t, J=7.5 Hz, 1H), 7.12 (m, 3H), 7.04 (d, J=9.5 Hz, 1H), 3.96 (m, 4H), 3.55 (m, J=6.72 and 13.2 Hz, 2H), 3.40 (m, 4H), 1.51 (dd, J=6.7 and 13.8 Hz, 2H), 0.74 (m, 1H), 0.45 (m, 2H), 0.08 (m, 2H). $^{13}$C NMR (75 MHz, CDCl$_3$) δ 162.9, 150.8, 145.2, 129.8, 127.2, 119.19, 116.75, 112.6, 48.5, 44.7, 39.7, 34.5, 8.7, 4.2.

EXAMPLE 2

Synthesis of 6-(4-Benzooxazol-2-Yl-Piperazin-1-Yl) Pyridazine-3-Carboxylic Acid (2-Cyclopropylethyl) Amide To the 6-piperazin-1-yl-pyridazine-3-carboxylic acid (2-cyclopropylethyl)amide (0.080 g, 0.290 mmol) in dioxane (7 mL) was added 2-chlorobenzooxazole (0.053 g, 0.34 mmol) followed by the addition of 1,8-diazabicyclo[5,4,0]undec-7-ene (0.132 mL, 0.87 mmol) and tetra-n-butylammonium iodide (3 mg). The reaction mixture was stirred at room temperature for 3 hours. The solvent was removed in vacuo. The residue was dissolved in ethyl acetate, then washed with citric acid, sodium bicarbonate and brine solution. The organic layer was separated, and dried over anhydrous Na$_2$SO$_4$, and evaporated. The residue was purified by recrystallization from n-hexane to yield the title compound as a white powder in 44% yield (0.050 g). $^1$H NMR (300 MHz, CDCl$_3$) δ 8.07 (d, J=9.5 Hz, 1H), 7.99 (t, J=5.3 Hz, 1H), 7.39 (d, J=7.4 Hz, 1H), 7.28 (d, J=7.8 Hz, 1H), 7.19 (m, 1H), 7.05 (m, 2H), 3.92 (m, 8H), 3.55 (m, 2H), 1.48 (m, 2H), 0.79 (m, 1H), 0.46 (m, 2H), 0.07 (m, 2H). MS (ES+) m/z 393 (M+1).

Example 2.1

Synthesis of 6-(4-Benzothiazol-2-Ylpiperazin-1-Yl) Pyridazine-3-Carboxylic Acid (2-Cyclopropylethyl) Amide Following the procedure as described in Example 2, making variation only as required to use 2-chlorobenzothiazole to replace 2-chlorobenzooxazole to react with 6-piperazin-1-yl-pyridazine-3-carboxylic acid (2-cyclopropylethyl)amide, the title compound was obtained as a white powder in 27% yield (0.040 g). $^1$H NMR (300 MHz, CDCl$_3$) δ 8.07 (d, J=9.5 Hz, 1H), 7.99 (t, J=5.4 Hz, 1H), 7.59 (m, 2H), 7.32 (t, J=6.5 Hz, 1H), 7.12 (t, J=8.2 Hz, 1H), 7.03 (d, J=9.4 Hz, 1H), 3.94 (m, 4H), 3.81 (m, 4H), 3.53 (m, 2H), 1.50 (m 2H), 0.75 (m, 1H), 0.45 (m, 2H), 0.06 (m, 2H). MS (ES+) m/z 409.2 (M+1).

Example 2.2

Synthesis of 6-(4-Quinazolin-4-Ylpiperazin-1-Yl) Pyridazine-3-Carboxylic Acid (2-Cyclopropylethyl) Amide Following the procedure as described in Example 2, making variation only as required to use 4-chloroquinzoline to replace 2-chlorobenzooxazole to react with 6-piperazin-1-yl-pyridazine-3-carboxylic acid (2-cyclopropylethyl)amide, the title compound was obtained as a white powder in 27% yield (40 mg). $^1$H NMR (300 MHz, CDCl$_3$) δ 8.76 (s, 1H), 8.06 (d, J=9.4 Hz, 1H), 7.95 (m, 3H), 7.77 (t, J=7.3 Hz, 1H), 7.50 (t, J=7.3 Hz, 1H), 7.01 (d, J=9.5 Hz, 1H), 3.98 (m, 8H), 3.55 (m, 2H), 1.5 (m, 2H), 0.74 (m, 1H), 0.43 (m, 2H), 0.08 (m, 2H). MS (ES+) m/z 403.67 (M+1).

EXAMPLE 3

Synthesis of 6-[4-(3-Oxo-3H-Isoindol-1-Yl)Piperazin-1-Yl]Pyridazine-3-Carboxylic Acid (2-Cyclopropylethyl)Amide 3-Aminoisoindol-1-one (0.292 g, 2.00 mmol) and 6-piperazin-1-ylpyridazine-3-carboxylic acid (2-cyclopropylethyl)amide (0.825 g, 3.00 mmol) were boiled together in ethanol (20 mL) for 48 hours. The solution was concentrated in vacuo. This residue was purified by column chromatography. The title compound was obtained as a white solid in 40% yield (0.328 g). $^1$H NMR (300 MHz, CDCl$_3$) δ 8.07 (d, J=9.5 Hz, 1H), 7.97 (t, J=5.8 Hz, 1H), 7.76 (d, J=7.0 Hz, 1H), 7.64 (d, J=7.3 Hz, 1H), 7.52 (m, 1H), 7.01 (d, J=9.5 Hz, 1H), 4.42-4.35 (m, 4H), 4.23-4.20 (m, 2H), 3.93-3.89 (m, 2H), 3.54 (dd, J=6.7 and 13.2 Hz, 1H), 1.49 (m, 1H), 0.79-0.66 (m, 1H), 0.47-0.41 (m, 2H), 0.10-0.05 (m, 2H). $^{13}$C NMR (75 MHz, CDCl$_3$) δ 181.5, 174.6, 162.9, 159.6, 145.6, 138.1, 134.9, 132.5, 131.7, 127.3, 124.0 123.3, 112.2, 47.2, 46.4 44.5, 43.2, 39.7, 34.5, 8.7, 4.2. MS (ES+) m/z 405.1 (M+1).

EXAMPLE 4

Measuring Stearoyl-CoA Desaturase Inhibition Activity of a Test Compound Using Mouse Liver Microsomes The identification of compounds of the invention as SCD inhibitors was readily accomplished using the SCD enzymes and microsomal assay procedure described in Brownlie et al, PCT published patent application, WO 01/62954.
Preparation of Mouse Liver Microsomes:

Male ICR mice, on a high-carbohydrate, low fat diet, under light halothane (15% in mineral oil) anesthesia are sacrificed by exsanguination during periods of high enzyme activity. Livers are immediately rinsed with cold 0.9% NaCl solution, weighed and minced with scissors. All procedures are performed at 4° C. unless specified otherwise. Livers are homogenized in a solution (1:3 w/v) containing 0.25 M sucrose, 62 mM potassium phosphate buffer (pH 7.0), 0.15 M KCl, 1.5 mM N-acetyleysteine, 5 mM $MgCl_2$, and 0.1 mM EDTA using 4 strokes of a Potter-Elvehjem tissue homogenizer. The homogenate is centrifuged at 10,400×g for 20 min to eliminate mitochondria and cellular debris. The supernatant is filtered through a 3-layer cheesecloth and centrifuged at 105,000×g for 60 min. The microsomal pellet is gently resuspended in the same homogenization solution with a small glass/teflon homogenizer and stored at −70° C. The absence of mitochondrial contamination is enzymatically assessed. The protein concentration is measured using bovine serum albumin as the standard.
Incubation of Mouse Liver Microsomes with Test Compounds:

Reactions are started by adding 2 mg of microsomal protein to pre-incubated tubes containing 0.20 μCi of the substrate fatty acid (1-$^{14}$C palmitic acid) at a final concentration of 33.3 μM in 1.5 ml of homogenization solution, containing 42 mM NaF, 0.33 mM niacinamide, 1.6 mM ATP, 1.0 mM NADH, 0.1 mM coenzyme A and a 10 μM concentration of test compound. The tubes are vortexed vigorously and after 15 min incubation in a shaking water bath (37° C.), the reactions are stopped and fatty acids are analyzed.

Fatty acids are analyzed as follows: The reaction mixture is saponified with 10% KOH to obtain free fatty acids which are further methylated using $BF_3$ in methanol. The fatty acid methyl esters are analyzed by high performance liquid chromatography (HPLC) using a Hewlett Packard 1090, Series II chromatograph equipped with a diode array detector set at 205 nm, a radioisotope detector (Model 171, Beckman, Calif.) with a solid scintillation cartridge (97% efficiency for $^{14}$C-detection) and a reverse-phase ODS (C-18) Beckman column (250 mm×4.6 mm i.d.; 5 μm particle size) attached to a pre-column with a μBondapak C-18 (Beckman) insert. Fatty acid methyl esters are separated isocratically with acetonitrile/water (95:5 v:v) at a flow rate of 1 mL/min and are identified by comparison with authentic standards. Alternatively, fatty acid methyl esters may be analyzed by capillary column gas-chromatography (GC) or Thin Layer Chromatography (TLC).

Those skilled in the art are aware of a variety of modifications to this assay that can be useful for measuring inhibition of stearoyl-CoA desaturase activity in microsomes by test compounds.

Representative compounds of the invention showed activity as inhibitors of SCD when tested in this assay. The activity was defined in terms of % SCD enzyme activity remaining at the desired concentration of the test compound.

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of inhibiting human stearoyl-CoA desaturase (hSCD) activity comprising contacting a source of hSCD with a compound of formula (Ia):

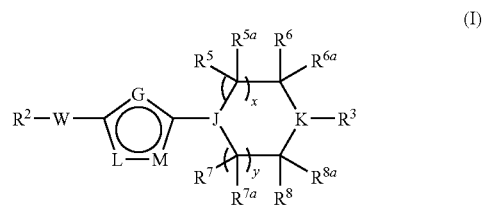

wherein:
x and y are each 1;
G is —C($R^4$)=C($R^4$)—;
L and M are both —N=;
W is —N($R^1$)C(O)—;
$R^1$ is hydrogen;
$R^2$ is selected from the group consisting of $C_7$-$C_{12}$alkyl, $C_2$-$C_{12}$alkenyl, $C_7$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_{13}$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;
$R^3$ is selected from the group consisting of $C_3$-$C_{12}$heterocyclyl, $C_1$-$C_{12}$heteroaryl and aryl optionally substituted by one or more substituents selected from the group consisting of alkyl, alkenyl, halo, haloalkyl, haloalkenyl, cyano, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—OC(O)—$R^{14}$, —$R^{15}$—C(O)$R^{14}$, —$R^{15}$—C(O)$OR^{14}$, —$R^{15}$—C(O)N($R^{14}$)$_2$, —$R^{15}$—N($R^{14}$)C(O)$R^{16}$, —$R^{15}$—N($R^{14}$)(S(O)$_t R^{16}$) (where t is 1 or 2), —$R^{15}$—S(O)$_t OR^{16}$ (where t is 1 or 2), —$R^{15}$—S(O)$_t R^{16}$ (where t is 0, 1 or 2), and —$R^{15}$—S(O)$_t N(R^{14})_2$ (where t is 1 or 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above optional substituents is unsubstituted;
each $R^4$ is hydrogen; and
$R^5$ $R^{5a}$, $R^6$, $R^{6a}$, $R^7$, $R^{7a}$, $R^8$ and $R^{8a}$ are each hydrogen;
provided that $R^2$ is not $C_5$-$C_{10}$pyrazinylalkyl, pyridinonyl, pyrrolidinonyl, methylimidazolyl or phenyl substituted with amino;
as a stereoisomer, enantiomer or tautomer thereof; or as a pharmaceutically acceptable salt thereof.

2. The method of claim 1 where $R^3$ is aryl optionally substituted by one or more substituents selected from the group consisting of alkyl, alkenyl, halo, haloalkyl, haloalkenyl, cyano, aryl, aralkyl, cycloalkyl, cycloalkylalkyl, heterocyclyl, heterocyclylalkyl, heteroaryl, heteroarylalkyl, $-R^{15}-OR^{14}$, $-R^{15}-OC(O)-R^{14}$, $-R^{15}-C(O)R^{14}$, $-R^{15}-C(O)OR^{14}$, $-R^{15}-C(O)N(R^{14})_2$, $-R^{15}-N(R^{14})C(O)R^{16}$, $-R^{15}-N(R^{14})(S(O)_tR^{16})$ (where t is 1 or 2), $-R^{15}-S(O)_tOR^{16}$ (where t is 1 or 2), $-R^{15}-S(O)_tR^{16}$ (where t is 0, 1 or 2), and $-R^{15}-S(O)_tN(R^{14})_2$ (where t is 1 or 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above optional substituents is unsubstituted.

3. The method of claim 1 wherein the compound of formula (Ia) is selected from the group consisting of:
   6-[4-(4-fluorophenyl)piperazin-1-yl]pyridazine-3-carboxylic acid (2-cyclopropylethyl)amide; and
   6-[4-(3-trifluoromethylphenyl)piperazin-1-yl]pyridazine-3-carboxylic acid (2-cyclopropylethyl)amide.

4. The method of claim 1 where $R^3$ is $C_1$-$C_{12}$ heteroaryl.

5. The method of claim 4 wherein the compound of formula (Ia) is selected from the group consisting of:
   6-(4-benzooxazol-2-yl-piperazin-1-yl)pyridazine-3-carboxylic acid (2-cyclopropylethyl)amide;
   6-(4-benzothiazol-2-yl-piperazin-1-yl)pyridazine-3-carboxylic acid (2-cyclopropylethyl)amide;
   6-(4-quinazolin-4-yl-piperazin-1-yl)pyridazine-3-carboxylic acid (2-cyclopropylethyl)amide;
   6-[4-(3-trifluoromethylpyridin-2-yl)-piperazin-1-yl]-pyridazine-3-carboxylic acid (2-cyclopropylethyl)amide;
   6-(4-benzo[d]isothiazol-3-yl-piperazin-1-yl)pyridazine-3-carboxylic acid (2-cyclopropylethyl)amide;
   6-(4-pyridin-2-yl-piperazin-1-yl)pyridazine-3-carboxylic acid (2-cyclopropylethyl)amide; and
   6-[4-(3-oxo-3H-isoindol-1-yl)piperazin-1-yl]pyridazine-3-carboxylic acid (2-cyclopropylethyl)amide.

* * * * *